(12) United States Patent
Kuklik et al.

(10) Patent No.: US 9,896,497 B2
(45) Date of Patent: Feb. 20, 2018

(54) TOLL-LIKE RECEPTOR 2 BINDING EPITOPE AND BINDING MEMBER THERETO

(71) Applicant: Opsona Therapeutics Limited, Dublin (IE)

(72) Inventors: Nils Kuklik, Essen (DE); Wolf-Dieter Schubert, Bellville (ZA)

(73) Assignee: Opsona Therapeutics Limited, Dublin (IE)

(*) Notice: Subject to any disclaimer, the term of this patent is extended or adjusted under 35 U.S.C. 154(b) by 175 days.

(21) Appl. No.: 14/384,824

(22) PCT Filed: Mar. 29, 2013

(86) PCT No.: PCT/EP2013/056824
§ 371 (c)(1),
(2) Date: Sep. 12, 2014

(87) PCT Pub. No.: WO2013/144345
PCT Pub. Date: Oct. 3, 2013

(65) Prior Publication Data
US 2015/0023974 A1 Jan. 22, 2015

(30) Foreign Application Priority Data
Mar. 30, 2012 (GB) .................................. 1205633.9

(51) Int. Cl.
| | | |
|---|---|---|
| *C07K 14/705* | (2006.01) | |
| *G01N 33/53* | (2006.01) | |
| *G01N 33/566* | (2006.01) | |
| *G01N 33/68* | (2006.01) | |
| *C07K 16/28* | (2006.01) | |
| *A61K 38/17* | (2006.01) | |
| *G06F 19/16* | (2011.01) | |
| *A61K 47/68* | (2017.01) | |
| *A61K 39/00* | (2006.01) | |

(52) U.S. Cl.
CPC ...... *C07K 14/70596* (2013.01); *A61K 38/177* (2013.01); *A61K 47/6849* (2017.08); *C07K 14/705* (2013.01); *C07K 16/2896* (2013.01); *G01N 33/53* (2013.01); *G06F 19/16* (2013.01); *A61K 39/00* (2013.01); *C07K 2317/24* (2013.01); *C07K 2317/34* (2013.01); *C07K 2317/55* (2013.01); *C07K 2317/76* (2013.01); *C07K 2319/70* (2013.01); *G01N 33/566* (2013.01); *G01N 33/68* (2013.01); *G01N 2333/705* (2013.01); *G01N 2333/70596* (2013.01)

(58) Field of Classification Search
CPC ...... A61K 38/00; A61K 38/17; A61K 38/177; A61K 38/1703; A61K 38/1709; C07K 14/705; C07K 14/70596; C07K 14/47; C07K 38/16; G01N 33/68; G01N 33/56; G01N 2333/705; G01N 2333/70596
See application file for complete search history.

(56) References Cited

U.S. PATENT DOCUMENTS

| 8,734,794 B2 | 5/2014 | Dellacasagrande | |
|---|---|---|---|
| 2005/0124538 A1* | 6/2005 | Schiffrin .............. | C07K 14/705 435/69.1 |

FOREIGN PATENT DOCUMENTS

| EP | 2451842 B1 * | 7/2010 |
|---|---|---|
| EP | 2722342 A1 * | 10/2012 |
| WO | 2005028509 | 3/2005 |
| WO | 2008132516 | 11/2008 |
| WO | 2009031834 | 3/2009 |

OTHER PUBLICATIONS

Arslan et al. Myocardial ischemia/reperfusion injury is mediated by leukocytic toll-like receptor-2 and reduced by systemic administration of a novel anti-toll-like receptor-2 antibody. Circulation 121: 80-90, 2010.*
Arslan et al. Treatment with OPN-305, a humanized anti-toll-like receptor-2 antibody, reduces myocardial ischemia/reperfusion injury in pigs. Cardiovasc Inter 5: 279-287, 2012.*
Dulay et al. Soluble TLR2 is present in human amniotic fluid and modulates the intraamniotic response to infection. J Immunol 182: 7244-7253, 2009.*
LeBouder et al. Soluble forms of toll-like receptor (TLR)2 capable of modulating TLR2 signaling are present in human plasma and breast milk. J Immunol 171: 6680-6689, 2003.*
Matsushima et al. Comparative sequence analysis of leucine-rich repeats (LRRs) within vertebrate toll-like receptors. BMC Genomics 8: 124, 2007.*
Raby et al. Soluble TLR2 reduces inflammation without compromising bacterial clearance by disrupting TLR2 triggering. J Immunol 183: 506-517, 2009.*
Savva et al. Targeting toll-like receptors: promising therapeutic strategies for the management of sepsis-associated pathology and infectious diseases. Frontiers Immunol 4: 387, 2013.*

(Continued)

*Primary Examiner* — Bridget E Bunner
(74) *Attorney, Agent, or Firm* — Workman Nydegger

(57) ABSTRACT

The present invention relates to the identification of a TLR2 binding epitope wherein binding of a binding member to the epitope serves to inhibit TLR2 activation and/or signalling. Polypeptide fragments of TLR2 and three-dimensional structures comprising one or more amino acid residues His318, Pro320, Gln321 or Arg321, Tyr323, Lys347, Phe349, Leu371, Glu375, Tyr376 and His398 of TLR2 which define the identified epitope are provided for use in generating binding members. Also provided are binding members which bind to the identified epitope and methods of using same for the treatment and/or prevention of conditions associated with TLR2 activation and/or signalling.

11 Claims, 25 Drawing Sheets

(19 of 25 Drawing Sheet(s) Filed in Color)

(56) References Cited

OTHER PUBLICATIONS

"Vaccine" definition entry; downloaded from Stedman's Medical Dictionary 28$^{th}$ Edition on Jun. 30, 2011; pp. 1-3.*

"Vaccine" definition entry; downloaded from Britannica Online Encyclopedia on Jun. 30, 2011; pp. 1-2.*

International Search Report and Written Opinion, PCT/EP2013/056824, dated Jan. 10, 2013.

Guangxun Meng: "Antagonistic antibody prevents toll-like receptor 2-driven lethal shock-like syndromes", Journal of Clinical Investigation, American Society for Clinical Investigation, US, vol. 113, No. 10, May 15, 2004 (May 15, 2004), pp. 1473-1481. Retrieved from the Internet on Aug. 28, 2014: http://www.jci.org/articles/view/20762.

Nils Kuklik: "Structural analysis of the specific inactivation of Toll-like receptor 2", Jul. 11, 2012 (Jul. 11, 2012), pp. 1-124, Retrieved from the Internet on Aug. 28, 2014: http://digisrv-1.biblio.etc.tu-bs.de:8080/docportal/servlets/MCRFileNodeServlet/DocPortal_derivate_00026577/Dissertation_Nils-Kuklik_2012.pdf;jsessionid=635F6E49DC228D9A6D1A1F1D48EB190E.

International Preliminary Report on Patentability from International Application No. PCT/EP2013/056824 dated Oct. 9, 2014 (12pages).

* cited by examiner

A
| | | |
|---|---|---|
| Fab$_{light}$ | 23817.77 Da | |
| | ÷ | = 47454.46 Da + 2 H⁺ (1 H⁺ per chain, MS artifact) |
| Fab$_{heavy}$ Q$^1$-G$^{221}$ | 23636.69 Da | = 47456.46 Da |
| | | |
| Fab$_{light}$ | 23817.77 Da | |
| | ÷ | = 47019.24 Da + 2 H⁺ (1 H⁺ per chain, MS artifact) |
| Fab$_{heavy}$ Q$^1$-E$^{217}$ | 23201.47 Da | = 47021.24 Da |

B  Heavy Chain Cleavage Sites

```
        10         20         30         40         50         60
    QVQLVQSGSE LKKPGASVKL SCKASGFTFT TYGINWVRQA PGQGLEWIGW IYPRDGSTNF
        70         80         90        100        110        120
    NENFKDRATI TVDTSASTAY MELSSLRSED TAVYFCARLT GGTFLDYWGQ GTTVTVSSAS
       130        140        150        160        170        180
    TKGPSVFPLA PCSRSTSEST AALGCLVKDY FPEPVTVSWN SGALTSGVHT FPAVLQSSGL
       190        200        210        220
    YSLSSVVTVP SSSLGTKTYT CNVDHKPSNT KVDKRVESKY GPPCPPCPA
                                        ↑     ↑
                                          ↑ ↑
```

Figure 8

```
LRR11|human    DPGKVETLTIRRLI  F LFYDLSTLYS  333
     |mouse    ELGKVETVTIRRLI  F LFYDLSTVYS  333
     |monkey   DPGKVETVTIRRLI  F SFNDLSTLYP  333
     |pig      SLGNVETLTVRRLI   FFLFYDLRSIYS 334
              . *:***:*:******:*: * ** ::*.

LRR12|human    LIERVKRITVENS V LVPCLLSQ      357
     |mouse    LLEKVKRITVENS V LVPCSFSQ      357
     |monkey   LTERVKRITVENS V LVPCLLSR      357
     |pig      LTGAVKRITIENS V LVPCSLSQ      358
              *    *****:********** :*:

LRR13|human    HLKSLEYLDLSEN MVE LKNSACED      384
     |mouse    HLKSLEFLDLSEN MVE LKNSACKG      384
     |monkey   HLKSLEYLDLSEN MVE LKNSACED      384
     |pig      HLKSLEYLDLSEN MSE LKNSACEH      385
              ******:******** *********:

LRR14|human    AWPSLQTLILRQN LASLEKTGETLL      410
     |mouse    AWPSLQTLVLSQN LRSMQKTGEILL      410
     |monkey   AWPSLQTLILRQN LASLGKTGETLL      410
     |pig      AWPFLHTLILRQN LKSLEKTGEVLV      411
              *** *:**:* **** *: **** *:
```

▨ Presumed antibody interaction
▨ Dimerization with TLR1 / TLR6

Figure 19

```
ATOM   2275  N   HIS A 318      26.518   1.172   6.935  1.00 21.01           N
ATOM   2276  CA  HIS A 318      27.871   0.897   6.468  1.00 22.29           C
ATOM   2277  C   HIS A 318      28.791   0.540   7.626  1.00 22.84           C
ATOM   2278  O   HIS A 318      29.001   1.347   8.534  1.00 22.75           O
ATOM   2279  CB  HIS A 318      28.435   2.109   5.718  1.00 22.74           C
ATOM   2280  CG  HIS A 318      29.890   1.987   5.389  1.00 26.01           C
ATOM   2281  ND1 HIS A 318      30.510   0.770   5.195  1.00 26.74           N
ATOM   2282  CD2 HIS A 318      30.844   2.928   5.204  1.00 24.90           C
ATOM   2283  CE1 HIS A 318      31.784   0.968   4.906  1.00 26.21           C
ATOM   2284  NE2 HIS A 318      32.012   2.269   4.904  1.00 28.34           N
ATOM   2293  N   PRO A 320      32.494  -0.358   8.009  1.00 34.22           N
ATOM   2294  CA  PRO A 320      33.822  -0.413   7.386  1.00 39.23           C
ATOM   2295  C   PRO A 320      34.599  -1.708   7.615  1.00 44.01           C
ATOM   2296  O   PRO A 320      34.807  -2.489   6.686  1.00 45.23           O
ATOM   2297  CB  PRO A 320      34.531   0.798   7.985  1.00 37.54           C
ATOM   2298  CG  PRO A 320      33.419   1.777   8.148  1.00 36.22           C
ATOM   2299  CD  PRO A 320      32.310   0.919   8.723  1.00 34.63           C
ATOM   2300  N   GLN A 321      35.032  -1.937   8.848  1.00 48.85           N
ATOM   2301  CA  GLN A 321      35.791  -3.142   9.149  1.00 54.88           C
ATOM   2302  C   GLN A 321      35.138  -3.931  10.274  1.00 58.85           C
ATOM   2303  O   GLN A 321      35.342  -3.649  11.456  1.00 58.50           O
ATOM   2304  CB  GLN A 321      37.232  -2.771   9.505  1.00 54.63           C
ATOM   2305  CG  GLN A 321      37.976  -2.099   8.356  1.00 54.27           C
ATOM   2306  CD  GLN A 321      39.415  -1.770   8.696  1.00 54.18           C
ATOM   2307  OE1 GLN A 321      39.686  -1.015   9.628  1.00 54.57           O
ATOM   2308  NE2 GLN A 321      40.347  -2.336   7.937  1.00 53.98           N
ATOM   2320  N   TYR A 323      35.810  -6.772  11.261  1.00 73.13           N
ATOM   2321  CA  TYR A 323      36.759  -7.578  12.019  1.00 75.88           C
ATOM   2322  C   TYR A 323      37.273  -6.805  13.232  1.00 77.38           C
ATOM   2323  O   TYR A 323      38.105  -7.304  13.995  1.00 78.06           O
ATOM   2324  CB  TYR A 323      37.926  -8.031  11.122  1.00 76.50           C
ATOM   2325  CG  TYR A 323      38.912  -6.957  10.706  1.00 77.93           C
ATOM   2326  CD1 TYR A 323      39.918  -6.525  11.574  1.00 78.09           C
ATOM   2327  CD2 TYR A 323      38.863  -6.399   9.429  1.00 78.41           C
ATOM   2328  CE1 TYR A 323      40.852  -5.566  11.176  1.00 78.50           C
ATOM   2329  CE2 TYR A 323      39.790  -5.440   9.022  1.00 78.54           C
ATOM   2330  CZ  TYR A 323      40.782  -5.029   9.899  1.00 78.72           C
ATOM   2331  OH  TYR A 323      41.702  -4.088   9.492  1.00 78.78           O
ATOM   2523  N   LYS A 347      24.548  -4.971   3.030  1.00 16.17           N
ATOM   2524  CA  LYS A 347      25.523  -6.013   2.710  1.00 18.85           C
ATOM   2525  C   LYS A 347      25.505  -7.227   3.631  1.00 19.28           C
ATOM   2526  O   LYS A 347      26.550  -7.799   3.952  1.00 18.64           O
ATOM   2527  CB  LYS A 347      26.926  -5.400   2.674  1.00 22.90           C
ATOM   2528  CG  LYS A 347      27.051  -4.280   1.652  1.00 26.45           C
ATOM   2529  CD  LYS A 347      28.312  -3.469   1.863  1.00 33.23           C
ATOM   2530  CE  LYS A 347      28.319  -2.225   0.978  1.00 35.40           C
ATOM   2531  NZ  LYS A 347      29.510  -1.368   1.240  1.00 37.66           N
ATOM   2539  N   PHE A 349      25.111 -10.997   4.494  1.00 16.89           N
ATOM   2540  CA  PHE A 349      25.232 -12.244   3.743  1.00 17.80           C
ATOM   2541  C   PHE A 349      24.979 -13.427   4.652  1.00 17.99           C
```

Figure 23A

```
ATOM   2542  O   PHE A 349      24.906 -14.574   4.198  1.00 17.64           O
ATOM   2543  CB  PHE A 349      26.621 -12.368   3.101  1.00 20.76           C
ATOM   2544  CG  PHE A 349      27.723 -12.679   4.072  1.00 23.75           C
ATOM   2545  CD1 PHE A 349      27.981 -13.994   4.461  1.00 26.20           C
ATOM   2546  CD2 PHE A 349      28.526 -11.660   4.576  1.00 27.06           C
ATOM   2547  CE1 PHE A 349      29.031 -14.288   5.335  1.00 26.57           C
ATOM   2548  CE2 PHE A 349      29.578 -11.942   5.451  1.00 28.03           C
ATOM   2549  CZ  PHE A 349      29.830 -13.258   5.829  1.00 28.39           C
ATOM   2718  N   LEU A 371      22.967  -9.625   0.411  1.00 15.62           N
ATOM   2719  CA  LEU A 371      23.766 -10.598  -0.332  1.00 17.50           C
ATOM   2720  C   LEU A 371      23.479 -12.056   0.012  1.00 16.46           C
ATOM   2721  O   LEU A 371      24.367 -12.905  -0.085  1.00 17.16           O
ATOM   2722  CB  LEU A 371      25.255 -10.307  -0.092  1.00 17.65           C
ATOM   2723  CG  LEU A 371      25.924  -9.053  -0.681  1.00 23.28           C
ATOM   2724  CD1 LEU A 371      25.065  -7.828  -0.492  1.00 28.79           C
ATOM   2725  CD2 LEU A 371      27.284  -8.858  -0.001  1.00 23.03           C
ATOM   2750  N   GLU A 375      23.145 -21.246   0.405  1.00 20.28           N
ATOM   2751  CA  GLU A 375      24.024 -21.893   1.389  1.00 22.45           C
ATOM   2752  C   GLU A 375      24.064 -21.193   2.740  1.00 20.03           C
ATOM   2753  O   GLU A 375      24.098 -21.849   3.781  1.00 19.35           O
ATOM   2754  CB  GLU A 375      25.454 -22.001   0.861  1.00 29.18           C
ATOM   2755  CG  GLU A 375      25.644 -22.987  -0.275  1.00 38.34           C
ATOM   2756  CD  GLU A 375      26.951 -23.751  -0.147  1.00 44.57           C
ATOM   2757  OE1 GLU A 375      27.392 -24.360  -1.149  1.00 46.70           O
ATOM   2758  OE2 GLU A 375      27.529 -23.752   0.964  1.00 46.52           O
ATOM   2759  N   TYR A 376      24.069 -19.864   2.725  1.00 17.30           N
ATOM   2760  CA  TYR A 376      24.110 -19.119   3.971  1.00 16.38           C
ATOM   2761  C   TYR A 376      22.722 -18.962   4.576  1.00 15.61           C
ATOM   2762  O   TYR A 376      22.581 -18.912   5.797  1.00 15.29           O
ATOM   2763  CB  TYR A 376      24.800 -17.765   3.756  1.00 15.66           C
ATOM   2764  CG  TYR A 376      26.263 -17.944   3.394  1.00 18.64           C
ATOM   2765  CD1 TYR A 376      26.647 -18.181   2.078  1.00 20.08           C
ATOM   2766  CD2 TYR A 376      27.249 -17.973   4.382  1.00 19.97           C
ATOM   2767  CE1 TYR A 376      27.983 -18.449   1.746  1.00 21.34           C
ATOM   2768  CE2 TYR A 376      28.593 -18.243   4.063  1.00 18.01           C
ATOM   2769  CZ  TYR A 376      28.944 -18.480   2.742  1.00 20.37           C
ATOM   2770  OH  TYR A 376      30.253 -18.760   2.408  1.00 21.55           O
ATOM   2911  N   GLN A 396      15.438  -8.287  -2.840  1.00 24.64           N
ATOM   2912  CA  GLN A 396      16.583  -8.136  -3.738  1.00 23.04           C
ATOM   2913  C   GLN A 396      17.885  -8.739  -3.220  1.00 17.55           C
ATOM   2914  O   GLN A 396      18.768  -8.024  -2.770  1.00 17.44           O
ATOM   2915  CB  GLN A 396      16.744  -6.643  -4.061  1.00 23.09           C
ATOM   2916  CG  GLN A 396      17.805  -6.284  -5.093  1.00 29.95           C
ATOM   2917  CD  GLN A 396      17.423  -5.052  -5.893  1.00 35.44           C
ATOM   2918  OE1 GLN A 396      16.531  -5.104  -6.743  1.00 36.92           O
ATOM   2919  NE2 GLN A 396      18.086  -3.932  -5.617  1.00 36.69           N
ATOM   2920  N   ASN A 397      17.990 -10.066  -3.277  1.00 16.12           N
ATOM   2921  CA  ASN A 397      19.201 -10.751  -2.836  1.00 14.94           C
ATOM   2922  C   ASN A 397      19.845 -11.571  -3.957  1.00 14.91           C
ATOM   2923  O   ASN A 397      19.691 -11.241  -5.128  1.00 14.81           O
ATOM   2924  CB  ASN A 397      18.906 -11.625  -1.618  1.00 14.06           C
ATOM   2925  CG  ASN A 397      18.760 -10.804  -0.347  1.00 14.11           C
ATOM   2926  OD1 ASN A 397      17.691 -10.249  -0.064  1.00 16.39           O
```

Figure 23B

```
ATOM   2927  ND2 ASN A 397      19.844 -10.694   0.407  1.00 11.73           N
ATOM   2928  N   HIS A 398      20.565 -12.630  -3.610  1.00 14.82           N
ATOM   2929  CA  HIS A 398      21.233 -13.446  -4.625  1.00 17.09           C
ATOM   2930  C   HIS A 398      20.765 -14.891  -4.713  1.00 15.59           C
ATOM   2931  O   HIS A 398      21.548 -15.780  -5.045  1.00 15.53           O
ATOM   2932  CB  HIS A 398      22.754 -13.411  -4.411  1.00 19.49           C
ATOM   2933  CG  HIS A 398      23.385 -12.110  -4.795  1.00 23.76           C
ATOM   2934  ND1 HIS A 398      23.090 -10.923  -4.162  1.00 30.45           N
ATOM   2935  CD2 HIS A 398      24.282 -11.809  -5.763  1.00 28.41           C
ATOM   2936  CE1 HIS A 398      23.781  -9.944  -4.723  1.00 28.62           C
ATOM   2937  NE2 HIS A 398      24.511 -10.455  -5.696  1.00 30.48           N
```

Figure 23C

SEQUENCE LISTING

<160> NUMBER OF SEQ ID NOS: 25

<210> SEQ ID NO 1

```
<211> LENGTH: 10
<212> TYPE: PRT
<213> ORGANISM: Artificial Sequence
<220> FEATURE:
<223> OTHER INFORMATION: amino acids at binding epitope on human TLR2

<400> SEQUENCE: 1

His Pro Arg Tyr Lys Phe Leu Glu Tyr His
1               5                   10

<210> SEQ ID NO 2
<211> LENGTH: 10
<212> TYPE: PRT
<213> ORGANISM: Artificial Sequence
<220> FEATURE:
<223> OTHER INFORMATION: amino acids at binding epitope on murine TLR2

<400> SEQUENCE: 2

His Pro Gln Tyr Lys Phe Leu Glu Tyr His
1               5                   10

<210> SEQ ID NO 3
<211> LENGTH: 784
<212> TYPE: PRT
<213> ORGANISM: Homo sapiens

<400> SEQUENCE: 3

Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255
```

```
Arg Asn Val Lys Ile Thr Asp Glu Ser Leu Phe Gln Val Met Lys Leu
        260                 265                 270

Leu Asn Gln Ile Ser Gly Leu Glu Leu Glu Phe Asp Asp Cys Thr
        275                 280                 285

Leu Asn Gly Val Gly Asn Phe Arg Ala Ser Asp Asn Asp Arg Val Ile
        290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
        340                 345                 350

Cys Leu Leu Ser Gln His Leu Lys Ser Leu Glu Tyr Leu Asp Leu Ser
        355                 360                 365

Glu Asn Leu Met Val Glu Tyr Leu Lys Asn Ser Ala Cys Glu Asp
    370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
        420                 425                 430

Gln Trp Pro Glu Lys Met Lys Tyr Leu Asn Leu Ser Ser Thr Arg Ile
        435                 440                 445

His Ser Val Thr Gly Cys Ile Pro Lys Thr Leu Glu Ile Leu Asp Val
        450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
        500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
        530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
        580                 585                 590

Gly Met Cys Cys Ala Leu Phe Leu Leu Ile Leu Leu Thr Gly Val Leu
        595                 600                 605

Cys His Arg Phe His Gly Leu Trp Tyr Met Lys Met Met Trp Ala Trp
        610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
        660                 665                 670
```

```
Cys Leu His Lys Arg Asp Phe Ile Pro Gly Lys Trp Ile Asp Asn
            675                 680                 685

Ile Ile Asp Ser Ile Glu Lys Ser His Lys Thr Val Phe Val Leu Ser
690                 695                 700

Glu Asn Phe Val Lys Ser Glu Trp Cys Lys Tyr Glu Leu Asp Phe Ser
705                 710                 715                 720

His Phe Arg Leu Phe Asp Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
            755                 760                 765

Ala Gln Arg Glu Gly Phe Trp Val Asn Leu Arg Ala Ala Ile Lys Ser
770                 775                 780

<210> SEQ ID NO 4
<211> LENGTH: 784
<212> TYPE: PRT
<213> ORGANISM: Mus musculus

<400> SEQUENCE: 4

Met Leu Arg Ala Leu Trp Leu Phe Trp Ile Leu Val Ala Ile Thr Val
1               5                   10                  15

Leu Phe Ser Lys Arg Cys Ser Ala Gln Glu Ser Leu Ser Cys Asp Ala
                20                  25                  30

Ser Gly Val Cys Asp Gly Arg Ser Arg Ser Phe Thr Ser Ile Pro Ser
            35                  40                  45

Gly Leu Thr Ala Ala Met Lys Ser Leu Asp Leu Ser Phe Asn Lys Ile
50                  55                  60

Thr Tyr Ile Gly His Gly Asp Leu Arg Ala Cys Ala Asn Leu Gln Val
65                  70                  75                  80

Leu Met Leu Lys Ser Ser Arg Ile Asn Thr Ile Glu Gly Asp Ala Phe
                85                  90                  95

Tyr Ser Leu Gly Ser Leu Glu His Leu Asp Leu Ser Asp Asn His Leu
            100                 105                 110

Ser Ser Leu Ser Ser Ser Trp Phe Gly Pro Leu Ser Ser Leu Lys Tyr
        115                 120                 125

Leu Asn Leu Met Gly Asn Pro Tyr Gln Thr Leu Gly Val Thr Ser Leu
    130                 135                 140

Phe Pro Asn Leu Thr Asn Leu Gln Thr Leu Arg Ile Gly Asn Val Glu
145                 150                 155                 160

Thr Phe Ser Glu Ile Arg Arg Ile Asp Phe Ala Gly Leu Thr Ser Leu
                165                 170                 175

Asn Glu Leu Glu Ile Lys Ala Leu Ser Leu Arg Asn Tyr Gln Ser Gln
            180                 185                 190

Ser Leu Lys Ser Ile Arg Asp Ile His His Leu Thr Leu His Leu Ser
        195                 200                 205

Glu Ser Ala Phe Leu Leu Glu Ile Phe Ala Asp Ile Leu Ser Ser Val
    210                 215                 220

Arg Tyr Leu Glu Leu Arg Asp Thr Asn Leu Ala Arg Phe Gln Phe Ser
225                 230                 235                 240

Pro Leu Pro Val Asp Glu Val Ser Ser Pro Met Lys Lys Leu Ala Phe
                245                 250                 255

Arg Gly Ser Val Leu Thr Asp Glu Ser Phe Asn Glu Leu Leu Lys Leu
            260                 265                 270
```

```
Leu Arg Tyr Ile Leu Glu Leu Ser Glu Val Glu Phe Asp Asp Cys Thr
        275                 280                 285

Leu Asn Gly Leu Gly Asp Phe Asn Pro Ser Glu Ser Asp Val Val Ser
        290                 295                 300

Glu Leu Gly Lys Val Glu Thr Val Thr Ile Arg Arg Leu His Ile Pro
305                 310                 315                 320

Gln Phe Tyr Leu Phe Tyr Asp Leu Ser Thr Val Tyr Ser Leu Leu Glu
                325                 330                 335

Lys Val Lys Arg Ile Thr Val Glu Asn Ser Lys Val Phe Leu Val Pro
                340                 345                 350

Cys Ser Phe Ser Gln His Leu Lys Ser Leu Glu Phe Leu Asp Leu Ser
                355                 360                 365

Glu Asn Leu Met Val Glu Glu Tyr Leu Lys Asn Ser Ala Cys Lys Gly
        370                 375                 380

Ala Trp Pro Ser Leu Gln Thr Leu Val Leu Ser Gln Asn His Leu Arg
385                 390                 395                 400

Ser Met Gln Lys Thr Gly Glu Ile Leu Leu Thr Leu Lys Asn Leu Thr
                405                 410                 415

Ser Leu Asp Ile Ser Arg Asn Thr Phe His Pro Met Pro Asp Ser Cys
                420                 425                 430

Gln Trp Pro Glu Lys Met Arg Phe Leu Asn Leu Ser Ser Thr Gly Ile
                435                 440                 445

Arg Val Val Lys Thr Cys Ile Pro Gln Thr Leu Glu Val Leu Asp Val
450                 455                 460

Ser Asn Asn Asn Leu Asp Ser Phe Ser Leu Phe Leu Pro Arg Leu Gln
465                 470                 475                 480

Glu Leu Tyr Ile Ser Arg Asn Lys Leu Lys Thr Leu Pro Asp Ala Ser
                485                 490                 495

Leu Phe Pro Val Leu Leu Val Met Lys Ile Arg Glu Asn Ala Val Ser
                500                 505                 510

Thr Phe Ser Lys Asp Gln Leu Gly Ser Phe Pro Lys Leu Glu Thr Leu
        515                 520                 525

Glu Ala Gly Asp Asn His Phe Val Cys Ser Cys Glu Leu Leu Ser Phe
        530                 535                 540

Thr Met Glu Thr Pro Ala Leu Ala Gln Ile Leu Val Asp Trp Pro Asp
545                 550                 555                 560

Ser Tyr Leu Cys Asp Ser Pro Pro Arg Leu His Gly His Arg Leu Gln
                565                 570                 575

Asp Ala Arg Pro Ser Val Leu Glu Cys His Gln Ala Ala Leu Val Ser
                580                 585                 590

Gly Val Cys Cys Ala Leu Leu Leu Ile Leu Leu Val Gly Ala Leu
                595                 600                 605

Cys His His Phe His Gly Leu Trp Tyr Leu Arg Met Met Trp Ala Trp
610                 615                 620

Leu Gln Ala Lys Arg Lys Pro Lys Lys Ala Pro Cys Arg Asp Val Cys
625                 630                 635                 640

Tyr Asp Ala Phe Val Ser Tyr Ser Glu Gln Asp Ser His Trp Val Glu
                645                 650                 655

Asn Leu Met Val Gln Gln Leu Glu Asn Ser Asp Pro Pro Phe Lys Leu
                660                 665                 670

Cys Leu His Lys Arg Asp Phe Val Pro Gly Lys Trp Ile Ile Asp Asn
                675                 680                 685
```

```
Ile Ile Asp Ser Ile Glu Lys Ser His Lys Thr Val Phe Val Leu Ser
            690                 695                 700
Glu Asn Phe Val Arg Ser Glu Trp Cys Lys Tyr Glu Leu Asp Phe Ser
705                 710                 715                 720
His Phe Arg Leu Phe Asp Glu Asn Asn Asp Ala Ala Ile Leu Val Leu
                725                 730                 735
Leu Glu Pro Ile Glu Arg Lys Ala Ile Pro Gln Arg Phe Cys Lys Leu
            740                 745                 750
Arg Lys Ile Met Asn Thr Lys Thr Tyr Leu Glu Trp Pro Leu Asp Glu
            755                 760                 765
Gly Gln Gln Glu Val Phe Trp Val Asn Leu Arg Thr Ala Ile Lys Ser
770                 775                 780
```

<210> SEQ ID NO 5
<211> LENGTH: 81
<212> TYPE: PRT
<213> ORGANISM: Homo sapiens

<400> SEQUENCE: 5

```
His Ile Pro Arg Phe Tyr Leu Phe Tyr Asp Leu Ser Thr Leu Tyr Ser
1               5                   10                  15
Leu Thr Glu Arg Val Lys Arg Ile Thr Val Glu Asn Ser Lys Val Phe
            20                  25                  30
Leu Val Pro Cys Leu Leu Ser Gln His Leu Lys Ser Leu Glu Tyr Leu
        35                  40                  45
Asp Leu Ser Glu Asn Leu Met Val Glu Glu Tyr Leu Lys Asn Ser Ala
    50                  55                  60
Cys Glu Asp Ala Trp Pro Ser Leu Gln Thr Leu Ile Leu Arg Gln Asn
65                  70                  75                  80
His
```

<210> SEQ ID NO 6
<211> LENGTH: 81
<212> TYPE: PRT
<213> ORGANISM: Mus musculus

<400> SEQUENCE: 6

```
His Ile Pro Gln Phe Tyr Leu Phe Tyr Asp Leu Ser Thr Val Tyr Ser
1               5                   10                  15
Leu Leu Glu Lys Val Lys Arg Ile Thr Val Glu Asn Ser Lys Val Phe
            20                  25                  30
Leu Val Pro Cys Ser Phe Ser Gln His Leu Lys Ser Leu Glu Phe Leu
        35                  40                  45
Asp Leu Ser Glu Asn Leu Met Val Glu Glu Tyr Leu Lys Asn Ser Ala
    50                  55                  60
Cys Lys Gly Ala Trp Pro Ser Leu Gln Thr Leu Val Leu Ser Gln Asn
65                  70                  75                  80
His
```

<210> SEQ ID NO 7
<211> LENGTH: 295
<212> TYPE: PRT
<213> ORGANISM: Homo sapiens

<400> SEQUENCE: 7

```
Val Gly Asn Phe Arg Ala Ser Asp Asn Asp Arg Val Ile Asp Pro Gly
1               5                   10                  15
```

Lys Val Glu Thr Leu Thr Ile Arg Arg Leu His Ile Pro Arg Phe Tyr
                20                  25                  30

Leu Phe Tyr Asp Leu Ser Thr Leu Tyr Ser Leu Thr Glu Arg Val Lys
            35                  40                  45

Arg Ile Thr Val Glu Asn Ser Lys Val Phe Leu Val Pro Cys Leu Leu
        50                  55                  60

Ser Gln His Leu Lys Ser Leu Glu Tyr Leu Asp Leu Ser Glu Asn Leu
65                  70                  75                  80

Met Val Glu Glu Tyr Leu Lys Asn Ser Ala Cys Glu Asp Ala Trp Pro
                85                  90                  95

Ser Leu Gln Thr Leu Ile Leu Arg Gln Asn His Leu Ala Ser Leu Glu
            100                 105                 110

Lys Thr Gly Glu Thr Leu Leu Thr Leu Lys Asn Leu Thr Asn Ile Asp
        115                 120                 125

Ile Ser Lys Asn Ser Phe His Ser Met Pro Glu Thr Cys Gln Trp Pro
130                 135                 140

Glu Lys Met Lys Tyr Leu Asn Leu Ser Ser Thr Arg Ile His Ser Val
145                 150                 155                 160

Thr Gly Cys Ile Pro Lys Thr Leu Glu Ile Leu Asp Val Ser Asn Asn
            165                 170                 175

Asn Leu Asn Leu Phe Ser Leu Asn Leu Pro Gln Leu Lys Glu Leu Tyr
        180                 185                 190

Ile Ser Arg Asn Lys Leu Met Thr Leu Pro Asp Ala Ser Leu Leu Pro
            195                 200                 205

Met Leu Leu Val Leu Lys Ile Ser Arg Asn Ala Ile Thr Thr Phe Ser
210                 215                 220

Lys Glu Gln Leu Asp Ser Phe His Thr Leu Lys Thr Leu Glu Ala Gly
225                 230                 235                 240

Gly Asn Asn Phe Ile Cys Ser Cys Glu Phe Leu Ser Phe Thr Gln Glu
            245                 250                 255

Gln Gln Ala Leu Ala Lys Val Leu Ile Asp Trp Pro Ala Asn Tyr Leu
        260                 265                 270

Cys Asp Ser Pro Ser His Val Arg Gly Gln Gln Val Gln Asp Val Arg
    275                 280                 285

Leu Ser Val Ser Glu Cys His
    290                 295

<210> SEQ ID NO 8
<211> LENGTH: 295
<212> TYPE: PRT
<213> ORGANISM: Mus musculus

<400> SEQUENCE: 8

Leu Gly Asp Phe Asn Pro Ser Glu Ser Asp Val Val Ser Glu Leu Gly
1               5                   10                  15

Lys Val Glu Thr Val Thr Ile Arg Arg Leu His Ile Pro Gln Phe Tyr
                20                  25                  30

Leu Phe Tyr Asp Leu Ser Thr Val Tyr Ser Leu Leu Glu Lys Val Lys
            35                  40                  45

Arg Ile Thr Val Glu Asn Ser Lys Val Phe Leu Val Pro Cys Ser Phe
        50                  55                  60

Ser Gln His Leu Lys Ser Leu Glu Phe Leu Asp Leu Ser Glu Asn Leu
65                  70                  75                  80

Met Val Glu Glu Tyr Leu Lys Asn Ser Ala Cys Lys Gly Ala Trp Pro
                85                  90                  95

```
Ser Leu Gln Thr Leu Val Leu Ser Gln Asn His Leu Arg Ser Met Gln
                100                 105                 110

Lys Thr Gly Glu Ile Leu Leu Thr Leu Lys Asn Leu Thr Ser Leu Asp
            115                 120                 125

Ile Ser Arg Asn Thr Phe His Pro Met Pro Asp Ser Cys Gln Trp Pro
130                 135                 140

Glu Lys Met Arg Phe Leu Asn Leu Ser Ser Thr Gly Ile Arg Val Val
145                 150                 155                 160

Lys Thr Cys Ile Pro Gln Thr Leu Glu Val Leu Asp Val Ser Asn Asn
                165                 170                 175

Asn Leu Asp Ser Phe Ser Leu Phe Leu Pro Arg Leu Gln Glu Leu Tyr
            180                 185                 190

Ile Ser Arg Asn Lys Leu Lys Thr Leu Pro Asp Ala Ser Leu Phe Pro
        195                 200                 205

Val Leu Leu Val Met Lys Ile Arg Glu Asn Ala Val Ser Thr Phe Ser
    210                 215                 220

Lys Asp Gln Leu Gly Ser Phe Pro Lys Leu Glu Thr Leu Glu Ala Gly
225                 230                 235                 240

Asp Asn His Phe Val Cys Ser Cys Glu Leu Leu Ser Phe Thr Met Glu
                245                 250                 255

Thr Pro Ala Leu Ala Gln Ile Leu Val Asp Trp Pro Asp Ser Tyr Leu
            260                 265                 270

Cys Asp Ser Pro Pro Arg Leu His Gly His Arg Leu Gln Asp Ala Arg
        275                 280                 285

Pro Ser Val Leu Glu Cys His
    290                 295

<210> SEQ ID NO 9
<211> LENGTH: 229
<212> TYPE: PRT
<213> ORGANISM: Homo sapiens

<400> SEQUENCE: 9

Gln Val Gln Leu Val Gln Ser Gly Ser Glu Leu Lys Lys Pro Gly Ala
1               5                   10                  15

Ser Val Lys Leu Ser Cys Lys Ala Ser Gly Phe Thr Phe Thr Thr Tyr
            20                  25                  30

Gly Ile Asn Trp Val Arg Gln Ala Pro Gly Gln Gly Leu Glu Trp Ile
        35                  40                  45

Gly Trp Ile Tyr Pro Arg Asp Gly Ser Thr Asn Phe Asn Glu Asn Phe
    50                  55                  60

Lys Asp Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Thr Gly Gly Thr Phe Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Pro Cys Pro Ala
225

<210> SEQ ID NO 10
<211> LENGTH: 29
<212> TYPE: PRT
<213> ORGANISM: Homo sapiens

<400> SEQUENCE: 10

Asp Pro Gly Lys Val Glu Thr Leu Thr Ile Arg Arg Leu His Ile Pro
1               5                   10                  15
Arg Phe Tyr Leu Phe Tyr Asp Leu Ser Thr Leu Tyr Ser
            20                  25

<210> SEQ ID NO 11
<211> LENGTH: 29
<212> TYPE: PRT
<213> ORGANISM: Mus musculus

<400> SEQUENCE: 11

Glu Leu Gly Lys Val Glu Thr Val Thr Ile Arg Arg Leu His Ile Pro
1               5                   10                  15
Gln Phe Tyr Leu Phe Tyr Asp Leu Ser Thr Val Tyr Ser
            20                  25

<210> SEQ ID NO 12
<211> LENGTH: 29
<212> TYPE: PRT
<213> ORGANISM: Macaca fascicularis

<400> SEQUENCE: 12

Asp Pro Gly Lys Val Glu Thr Val Thr Ile Arg Arg Leu His Ile Pro
1               5                   10                  15
Gln Phe Tyr Ser Phe Asn Asp Leu Ser Thr Leu Tyr Pro
            20                  25

<210> SEQ ID NO 13
<211> LENGTH: 29
<212> TYPE: PRT
<213> ORGANISM: Sus scrofa

<400> SEQUENCE: 13

Ser Leu Gly Asn Val Glu Thr Leu Thr Val Arg Arg Leu His Ile Pro
1               5                   10                  15
Gln Phe Phe Leu Phe Tyr Asp Leu Arg Ser Ile Tyr Ser
            20                  25

<210> SEQ ID NO 14
<211> LENGTH: 24
<212> TYPE: PRT
<213> ORGANISM: Homo sapiens

<400> SEQUENCE: 14

Leu Thr Glu Arg Val Lys Arg Ile Thr Val Glu Asn Ser Lys Val Phe
```

-continued

```
                1               5                   10                  15
Leu Val Pro Cys Leu Leu Ser Gln
            20

<210> SEQ ID NO 15
<211> LENGTH: 24
<212> TYPE: PRT
<213> ORGANISM: Mus musculus

<400> SEQUENCE: 15

Leu Leu Glu Lys Val Lys Arg Ile Thr Val Glu Asn Ser Lys Val Phe
1               5                   10                  15

Leu Val Pro Cys Ser Phe Ser Gln
            20

<210> SEQ ID NO 16
<211> LENGTH: 24
<212> TYPE: PRT
<213> ORGANISM: Macaca fascicularis

<400> SEQUENCE: 16

Leu Thr Glu Arg Val Lys Arg Ile Thr Val Glu Asn Ser Lys Val Phe
1               5                   10                  15

Leu Val Pro Cys Leu Leu Ser Arg
            20

<210> SEQ ID NO 17
<211> LENGTH: 24
<212> TYPE: PRT
<213> ORGANISM: Sus scrofa

<400> SEQUENCE: 17

Leu Thr Gly Ala Val Lys Arg Ile Thr Ile Glu Asn Ser Lys Val Phe
1               5                   10                  15

Leu Val Pro Cys Ser Leu Ser Gln
            20

<210> SEQ ID NO 18
<211> LENGTH: 27
<212> TYPE: PRT
<213> ORGANISM: Homo sapiens

<400> SEQUENCE: 18

His Leu Lys Ser Leu Glu Tyr Leu Asp Leu Ser Glu Asn Leu Met Val
1               5                   10                  15

Glu Glu Tyr Leu Lys Asn Ser Ala Cys Glu Asp
            20                  25

<210> SEQ ID NO 19
<211> LENGTH: 27
<212> TYPE: PRT
<213> ORGANISM: Mus musculus

<400> SEQUENCE: 19

His Leu Lys Ser Leu Glu Phe Leu Asp Leu Ser Glu Asn Leu Met Val
1               5                   10                  15

Glu Glu Tyr Leu Lys Asn Ser Ala Cys Lys Gly
            20                  25

<210> SEQ ID NO 20
<211> LENGTH: 27
<212> TYPE: PRT
```

```
<213> ORGANISM: Macaca fascicularis

<400> SEQUENCE: 20

His Leu Lys Ser Leu Glu Tyr Leu Asp Leu Ser Glu Asn Leu Met Val
1               5                   10                  15

Glu Glu Tyr Leu Lys Asn Ser Ala Cys Glu Asp
            20                  25

<210> SEQ ID NO 21
<211> LENGTH: 27
<212> TYPE: PRT
<213> ORGANISM: Sus scrofa

<400> SEQUENCE: 21

His Leu Lys Ser Leu Glu Tyr Leu Asp Leu Ser Glu Asn Leu Met Ser
1               5                   10                  15

Glu Glu Tyr Leu Lys Asn Ser Ala Cys Glu His
            20                  25

<210> SEQ ID NO 22
<211> LENGTH: 26
<212> TYPE: PRT
<213> ORGANISM: Homo sapiens

<400> SEQUENCE: 22

Ala Trp Pro Ser Leu Gln Thr Leu Ile Leu Arg Gln Asn His Leu Ala
1               5                   10                  15

Ser Leu Glu Lys Thr Gly Glu Thr Leu Leu
            20                  25

<210> SEQ ID NO 23
<211> LENGTH: 26
<212> TYPE: PRT
<213> ORGANISM: Mus musculus

<400> SEQUENCE: 23

Ala Trp Pro Ser Leu Gln Thr Leu Val Leu Ser Gln Asn His Leu Arg
1               5                   10                  15

Ser Met Gln Lys Thr Gly Glu Ile Leu Leu
            20                  25

<210> SEQ ID NO 24
<211> LENGTH: 26
<212> TYPE: PRT
<213> ORGANISM: Macaca fascicularis

<400> SEQUENCE: 24

Ala Trp Pro Ser Leu Gln Thr Leu Ile Leu Arg Gln Asn His Leu Ala
1               5                   10                  15

Ser Leu Gly Lys Thr Gly Glu Thr Leu Leu
            20                  25

<210> SEQ ID NO 25
<211> LENGTH: 26
<212> TYPE: PRT
<213> ORGANISM: Sus scrofa

<400> SEQUENCE: 25
```

```
Ala Trp Pro Phe Leu His Thr Leu Ile Leu Arg Gln Asn His Leu Lys
1               5                   10                  15
Ser Leu Glu Lys Thr Gly Glu Val Leu Val
                20              25
```

TOLL-LIKE RECEPTOR 2 BINDING EPITOPE AND BINDING MEMBER THERETO

FIELD OF THE INVENTION

The present invention relates to the identification of a binding epitope on Toll-like receptor 2 (TLR2) wherein binding of the epitope by a binding member can result in inhibition of the function of TLR2. The invention further extends to the use of the epitope in methods for generating binding members to the epitope and to binding members which bind to the epitope. The invention also extends to the use of said binding members in the treatment or prophylaxis of a disease which is mediated by TLR2 activation and/or signalling.

BACKGROUND TO THE INVENTION

Toll-like receptors (TLRs) form a family of pattern recognition receptors which have a key role in activating the innate immune response. 11 Toll-like receptors have been identified in humans to date. The members of the TLR family are highly conserved, with most mammalian species having between 10 to 15 TLRs. Each TLR recognises specific pathogen-associated molecular signatures. Toll-like receptor 2 (TLR2, CD282, TLR-2) is activated by peptidoglycan, lipoproteins and lipoteichoic acid.

TLRs are transmembrane proteins, in which a single-pass transmembrane α-helix connects the extracellular ligand-binding domain with the intracellular TIR domain. The extracellular domain (ECD) of TLRs is composed of 16-28 consecutive leucine rich repeat (LRR) units forming a bent, horseshoe-like shape. The LRRs stack on top of each other to create a helical or solenoid structure, in which conserved, mostly hydrophobic residues face inward to create a stable core. The conserved regions of consecutive LRRs (denoted by the amino acid sequence LXXLXLXXN, where L stands for leucine or other hydrophobic amino acids, X for any amino acid and N for asparagine) generate a hydrogen-bonded parallel β-sheet at the inner, concave surface of the molecular horseshoe. The variable parts composed of α-helixes and loops, due to their larger size, create the outer, convex surface. The LRR domain of TLRs is protected N- and C-terminal by two small capping modules known as LRR-NT and LRR-CT motifs, which contain cysteine clusters and shield the hydrophobic core formed by the β-sheet from exposure to the solvent.

Extracellular recognition of suitable molecular patterns leads to receptor dimerization which initiates intracellular signalling via cytoplasmic adaptor proteins such as MyD88 culminating in the translocation of the transcription factors (nuclear factor κB or NF-κB and interferon regulatory factor 3 and 7 or IRF3 and 7) into the nucleus and the activation of genes of the immune response. Ligand-induced dimerization of the extracellular domains places the C-termini of the receptors in close mutual proximity causing the transmembrane α-helices to align and the cytoplasmic TIR domains to interact triggering different intracellular signalling cascades. Depending on the ligand, TLR2 interacts with either TLR1 (triacylated lipopeptides) or TLR6 (diacetylated lipopeptides) to create two distinct heterodimers, TLR2/TLR1 and TLR2/TLR6. In both complexes, direct protein-protein interactions involve the central regions near the binding pockets.

In addition to microbial derived components, TLRs are also known to recognize damage-associated molecular patterns (DAMPs). These are host endogenous molecules released and distributed following stress, tissue damage and cellular disease. In cases in which the normal dampening of the immune response and the down-regulation of innate immunity is deregulated, persistent expression of pro-inflammatory cytokines can lead to inflammation and autoimmune diseases such as rheumatoid arthritis (RA), systemic lupus erythematosus (SLE), atherosclerosis and ischemia-reperfusion (I/R) injury. The immune response downstream of TLR2 has implicated TLR2 in many disease conditions. Accordingly, there is significant therapeutic interest in the modulation of the TLR2 signalling pathway and the development of TLR2 antagonists to inhibit cytokine production during inflammation and autoimmunity diseases has become of major interest.

In particular, antibodies have been developed having binding specificity to TLR2. For example, WO 2005/019431 discloses an antibody which has binding specificity to TLR2 designated 11G7. This murine antibody can be derived from hybridoma cell line 11G7 as deposited with the American Type Culture Centre (ATCC) under the designation PTA-5014. The 11G7 monoclonal antibody selectively binds to the extracellular domain of TLR2 and can block the induction of cytokine production by human peripheral blood mononuclear cells (PBMCs) stimulated with an agonist which activates a heterodimer formed between TLR1 and TLR2. The 11G7 antibody does not inhibit cytokine production by PBMCs stimulated with an agonist which induces signalling through a heterodimer formed between TLR6 and TLR2.

WO 2005/028509 discloses the murine T2.5 antibody (also known as OPN-301). This antibody is a murine IgG1 anti-TLR2 antibody which was derived from hybridoma clone T2.5 (HyCult Biotechnology b.v., Cell Sciences, Canton, USA: catalogue number 1054). WO 2005/028509 discloses that T2.5 or OPN-301 specifically inhibits the activation of mammalian TLR2 and cross-reacts with TLR2 from human, pig and monkey, indicating that the antibody is specific for a critical epitope. The T2.5 monoclonal antibody of WO 2005/028509 was raised against the extracellular domain of TLR2, and therefore has binding specificity to an epitope in that area of TLR2. WO 2005/028509 further discloses that the murine TL2.1 anti-TLR2 monoclonal antibody disclosed in WO 01/36488 is not cross-reactive to both human and murine forms of TLR2. Rather, the TL2.1 antibody is shown in WO 2005/028509 as binding only human TLR2 and not murine TLR2.

Several results have shown that TLR2 inhibition with T2.5 effectively reduces myocardial (I/R) injury and preserves cardiac function and geometry in vivo in mice and thus has the potential to be effective when administered to patients with acute myocardial infarction (MI). T2.5 also prevents pro-inflammatory cytokine release in rheumatoid arthritis (RA) tissue synovial explant cultures ex vivo. OPN-305 is a TLR2 specific monoclonal antibody which is a humanized version of T2.5 and which is described in WO2011/003925. OPN-305 was granted orphan status for the prevention of I/R injury associated with organ transplantation and is currently being tested in human trials. It would be desirable to generate further binding members having the same or similar functional properties as the T2.5 (OPN-301) and OPN-305 antibodies.

SUMMARY OF THE INVENTION

Following extensive experimentation, the present inventors have identified the TLR2 binding epitope to which the TLR2 antagonistic antibodies T2.5 (OPN-301) and OPN-305 specifically bind. Antibody binding to this epitope antagonises activation of the TLR2 receptor through heterodimer formation with either TLR1 or TLR6. Both fragments of TLR2 that delimit the epitope of TLR2 and three-dimensional structures directly revealing the epitope are useful in designing novel binding members that antagonise TLR2 activity analogously to T2.5 and OPN-305. Such binding members similarly inhibit TLR2-mediated signalling serving for the treatment and/or prevention of inflammation and disease conditions associated with TLR2 activation and/or signalling.

According to a first aspect of the present invention there is provided a polypeptide fragment of Toll-like receptor 2 (TLR2) comprising, consisting or consisting essentially of one or more amino acid residues His318 (H, histidine), Pro320 (P, proline), Gln321 (Q, glutamine) or Arg321 (R, arginine), Tyr323 (Y, tyrosine), Lys347 (K, lysine), Phe349 (F, phenylalanine), Leu371 (L, leucine), Glu375 (E, glutamic acid), Tyr376 (Y, tyrosine), and His398 (H, histidine) of TLR2 wherein said fragment of TLR2 is a fragment of TLR2 other than the extracellular domain of TLR2 and wherein at least said one or more amino acid residues His318, Pro320, Gln321 or Arg321, Tyr323, Lys347, Phe349, Leu371, Glu375, Tyr376 and His398 form a functional epitope in said fragment.

The epitope is a functional epitope for receptor dimerization or inhibition thereof. Typically the epitope is bound by the TLR2 antagonistic antibodies T2.5 and OPN-305. Binding of the identified epitope by a binding member, such as an antibody, results in antagonism of TLR2 biological function, in particular activation and signalling. In particular, binding by the binding member serves to inhibit activation of the TLR2 receptor, irrespective of whether a TLR2 heterodimer is formed with TLR1 or TLR6. Furthermore, antibodies binding to this epitope have been shown to cross-react with TLR2 from human, pig and monkey, indicating this to be a critical epitope in a highly conserved region of TLR2.

Typically the polypeptide fragment comprises at least two, three, four, five, six, seven, eight or nine or all of amino acid residues His318, Pro320, Gln321 or Arg321, Tyr323, Lys347, Phe349, Leu371, Glu375, Tyr376 and His398. Typically said at least two, three, four, five, six, seven, eight or nine or all amino acid residues His318, Pro320, Gln321 or Arg321, Tyr323, Lys347, Phe349, Leu371, Glu375, Tyr376 and His398 form the functional epitope in said fragment. The polypeptide fragment may comprise, consist or consist essentially of the amino acid residues His318, Pro320, Tyr323, Lys347, Phe349, Leu371, Glu375, Tyr376 and His398 in which case said amino acid residues form the epitope. The polypeptide fragment may comprise, consist or consist essentially of the amino acid residues His318, Pro320, Gln321, Tyr323, Lys347, Phe349, Leu371, Glu375, Tyr376 and His398 in which case said amino acid residues form the epitope. Other amino acid residues within the polypeptide fragment may also form part of the epitope. The polypeptide fragment may comprise, consist or consist essentially of the amino acid residues His318, Pro320, Arg321, Tyr323, Lys347, Phe349, Leu371, Glu375, Tyr376 and His398 in which case said amino acid residues form the epitope. In certain embodiments, the polypeptide fragment comprises, consists of or consists essentially of leucine rich repeat (LRR) regions 11 to 14 of TLR2 or a sequence which has at least 85%, 90% or 95% sequence homology thereto. Said LRRs may form the epitope. In certain embodiments, the polypeptide fragment comprises, consists of or consists essentially of leucine rich repeat (LRR) region 11 of TLR2 or a sequence which has at least 85%, 90% or 95% sequence homology thereto. Said LRR may form the epitope.

The fragment of TLR2 may be a fragment of human TLR2, murine TLR2, monkey TLR2, bovine TLR2, ovine TLR2 or any other mammalian TLR2. The full length human TLR2 sequence comprises 784 amino acids and is defined as Genbank Accession Number AAC 34133 (URL www.ncbi.nlm.nih.gov)). The full length murine TLR2 sequence comprises 784 amino acids and is defined as Genbank Accession Number NP_036035 (*Mus musculus*)).

```
(human TLR2)
                                                              SEQ ID NO: 3
MPHTLWMVWV LGVIISLSKE ESSNQASLSC DRNGICKGSS GSLNSIPSGL TEAVKSLDLS

NNRITYISNS DLQRCVNLQA LVLTSNGINT IEEDSFSSLG SLEHDLSYN  YLSNLSSSWF

KPLSSLTFLN LLGNPYKTLG ETSLFSHLTK LQILRVGNMD TFTKIQRKDF AGLTFLEELE

IDASDLQSYE PKSLKSIQNV SHLILHMKQH ILLLEIFVDV TSSVECLELR DTDLDTFHFS

ELSTGETNSL IKKFTFRNVK ITDESLFQVM KLLNQISGLL ELEFDDCTLN GVGNFRASDN

DRVIDPGKVE TLTIRRLHIP RFYLFYDLST LYSLTERVKR ITVENSKVFL VPCLLSQHLK

SLEYLDLSEN LMVEEYLKNS ACEDAWPSLQ TLILRQNHLA SLEKTGETLL

TLKNLTNIDI SKNSFHSMPE TCQWPEKMKY LNLSSTRIHS VTGCIPKTLE

ILDVSNNNLN LFSLNLPQLK ELYISRNKLM TLPDASLLPM LLVLKISRNA ITTFSKEQLD

SFHTLKTLEA GGNNFICSCE FLSFTQEQQA LAKVLIDWPA NYLCDSPSHV

RGQQVQDVRL SVSECHRTAL VSGMCCALFL LILLTGVLCH RFHGLWYMKM

MWAWLQAKRK PRKAPSRNIC YDAFVSYSER DAYWVENLMV QELENFNPPF

KLCLHKRDFI PGKWIIDNII DSIEKSHKTV FVLSENFVKS EWCKYELDFS HFRLFEENND

AAILILLEPI EKKAIPQRFC KLRKIMNTKT YLEWPMDEAQ REGFWVNLRA AIKS
```

(murine TLR2)
SEQ ID NO: 4

```
MLRALWLFWI LVAITVLFSK RCSAQESLSC DASGVCDGRS RSFTSIPSGL TAAMKSLDLS

FNKITYIGHG DLRACANLQV LMLKSSRINT IEGDAFYSLG SLEHLDLSDN HLSSLSSSWF

GPLSSLKYLN LMGNPYQTLG VTSLFPNLTN LQTLRIGNVE TFSEIRRIDF AGLTSLNELE

IKALSLRNYQ SQSLKSIRDI HHLTLHLSES AFLLEIFADI LSSVRYLELR DTNLARFQFS

PLPVDEVSSP MKKLAFRGSV LTDESFNELL KLLRYILELS EVEFDDCTLN GLGDFNPSES

DVVSELGKVE TVTIRRLHIP QFYLFYDLST VYSLLEKVKR ITVENSKVFL VPCSFSQHLK

SLEFLDLSEN LMVEEYLKNS ACKGAWPSLQ TLVLSQNHLR SMQKTGEILL

TLKNLTSLDI SRNTFHPMPD SCQWPEKMRF LNLSSTGIRV VKTCIPQTLE

VLDVSNNNLD SFSLFLPRLQ ELYISRNKLK TLPDASLFPV LLVMKIRENA VSTFSKDQLG

SFPKLETLEA GDNHFVCSCE LLSFTMETPA LAQILVDWPD SYLCDSPPRL

HGHRLQDARP SVLECHQAAL VSGVCCALLL LILLVGALCH HFHGLWYLRM

MWAWLQAKRK PKKAPCRDVC YDAFVSYSEQ DSHWVENLMV QQLENSDPPF

KLCLHKRDFV PGKWIIDNII DSIEKSHKTV FVLSENFVRS EWCKYELDFS

HFRLFDENND AAILVLLEPI ERKAIPQRFC KLRKIMNTKT YLEWPLDEGQ

QEVFWVNLRT AIKS
```

The fragment of TLR2 is not the extracellular domain of TLR2 or a C-terminal portion thereof. The term "extracellular domain" of TLR2 as used herein is understood to encompass fragments of TLR2 comprising amino acid residues 1-587, 1-570, 1-584, 221-587 and 292-586 of the polypeptide sequence of TLR2, in particular human or murine TLR2. The fragment of TLR2 of the invention does not therefore comprise amino acid residues 1-587, 1-570, 1-584, 221-587 or 292-586 of TLR2. Typically the fragment of TLR2 is an isolated or purified polypeptide.

Typically the fragment comprises, includes, consists essentially of or consists of less than 500, 400, 300, 290, 250, 200, 150, 140, 130, 125, 120, 115, 110, 109, 108, 107, 106, 105, 104, 103, 102, 101, 100, 99, 95, 90, 85, 84, 83, 82, 81 or 80 amino acids of the polypeptide sequence of TLR2, in particular human or murine TLR2. Typically the fragment comprises, includes, consists essentially of or consists of amino acid residues 250 to 450, 300 to 400, 310 to 412, 310 to 411, 311 to 412, 311 to 411, 311 to 398, 317 to 411, 317 to 398 or 318 to 398 of the polypeptide sequence of TLR2, in particular human or murine TLR2, e.g. of human TLR2 as shown in SEQ ID NO:3 or murine TLR2 as shown in SEQ ID NO:4, or a sequence which has at least 80%, 85%, 90%, 95%, 96%, 97%, 98% or 99% amino acid sequence identity with said amino acid residues of TLR2. Typically the fragment comprises, includes, consists essentially of or consists of less than amino acid residues 250 to 450, 300 to 400, 310 to 412, 310 to 411, 311 to 412, 310 to 411, 316 to 398 or 317 to 398 of the polypeptide sequence of TLR2, in particular human or murine TLR2, e.g. human TLR2 as shown in SEQ ID NO:3 or murine TLR2 as shown in SEQ ID NO:4, or a sequence which has at least 80%, 85%, 90%, 95%, 96%, 97%, 98% or 99% amino acid sequence identity with said amino acid residues of TLR2.

In addition to one, more or all of the epitope binding residues His318, Pro320, Gln321 or Arg321, Tyr323, Lys347, Phe349, Leu371, Glu375, Tyr376 and His398, the fragment may also include any complete region of secondary structure of TLR2 which contains these epitope binding residues. Accordingly, in certain embodiments the fragment includes Leu317 of TLR2, which is found at the beginning of the beta strand which contains His318. In certain embodiments, the fragment comprises, includes, consists essentially of or consists of amino acid residues Thr311 to Thr411 of the polypeptide sequence of TLR2, in particular human or murine TLR2, e.g. human TLR2 as shown in SEQ ID NO:3 or murine TLR2 as shown in SEQ ID NO:4, or a sequence which has at least 80%, 85%, 90%, 95%, 96%, 97%, 98% or 99% amino acid sequence identity with said amino acid residues of TLR2. This fragment contains complete elements of the secondary structures found before and after the epitope binding residues. The secondary structure of TLR2 is shown on the RCSB Protein Data Bank website. In certain embodiments, the fragment comprises, includes, consists essentially of or consists of less than amino acid residues Thr311 to Thr411 of the polypeptide sequence of TLR2, in particular human or murine TLR2, e.g. human TLR2 as shown in SEQ ID NO:3 or murine TLR2 as shown in SEQ ID NO:4, or a sequence which has at least 80%, 85%, 90%, 95%, 96%, 97%, 98% or 99% amino acid sequence identity with said amino acid residues of TLR2.

The sequence of amino acid residues 318 to 398 of human TLR2 is shown in SEQ ID NO:5 and the sequence of amino acid residues 318 to 398 of murine TLR2 is shown in SEQ ID NO:6.

Typically the sequence which has at least 80%, 85%, 90%, 95%, 96%, 97%, 98% or 99% amino acid sequence identity as referred to above comprises one or more of amino acid residues His318, Pro320, Gln321 or Arg321, Tyr323, Lys347, Phe349, Leu371, Glu375, Tyr376 and His398. Typically the sequence comprises at least two, three, four, five, six, seven, eight or nine or all of amino acid residues His318, Pro320, Gln321 or Arg321, Tyr323, Lys347, Phe349, Leu371, Glu375, Tyr376 and His398. In certain embodiments one or more amino acid residues are deleted or substituted. In particular, one or more amino acids may be substituted with a different natural amino acid, an amino acid derivative or a non-native amino acid.

Sequences may differ from those specified by one or more conservative amino acid substitutions, which typically have minimal influence on the secondary structure and hydrophobic nature of the polypeptide fragment. Sequences may also differ by one or more non-conservative amino acid substitutions, deletions or insertions which do not significantly alter the binding of OPN-301 or OPN-305 to the fragment. Conservative substitutions typically include the substitution of one amino acid for another with similar characteristics such as substitutions within the following groups: valine-glycine; glycine-alanine; valine-isoleucine; aspartic acid-glutamic acid; asparagine-glutamine; serine-threonine; lysine-arginine; and phenylalanine -tyrosine. In certain embodiments one or more amino acids may be added or inserted. In certain embodiments Gln321 or Arg321 is not present.

Typically the sequence which has at least 80% amino acid sequence identity has at least 85%, 90%, 91%, 92%, 93%, 94%, 95%, 96%, 97% 98% or 99% amino acid sequence identity. Typically binding of an antagonistic TLR2 antibody, such as OPN-301 or OPN-305, to the sequence results in antagonism of TLR2 activation and signalling. In particular, binding serves to inhibit activation of the TLR2 receptor, irrespective of whether a TLR2 heterodimer is formed with TLR1 or TLR6.

In certain embodiments the fragment comprises SEQ ID NO:1 or SEQ ID NO:2. SEQ ID NO:1 (HPRYKFLEYH) shows the amino acid residues of human TLR2 which form the binding residues in the functional conformational epitope in said fragment. SEQ ID NO:2 (HPQYKFLEYH) shows the amino acid residues of murine TLR2 which form the binding residues in the functional conformational epitope in said fragment.

Typically structure coordinates of said one or more amino acid residues His318, Pro320, Gln321 or Arg321, Tyr323, Lys347, Phe349, Leu371, Glu375, Tyr376 and His398 in the fragment are the same as structure coordinates of said one or more amino acid residues His318, Pro320, Gln321 or Arg321, Tyr323, Lys347, Phe349, Leu371, Glu375, Tyr376 and His398 in TLR2. Preferably, the structure coordinates are the same as structure coordinates of said amino acid residues in TLR2 when TLR2 is a monomer. In alternative embodiments, the structure coordinates are the same as structure coordinates of said amino acid residues in TLR2 when TLR2 has formed a heterodimer, e.g. with TLR1 or TLR6. In certain embodiments, the structure coordinates are the same as structure coordinates of said amino acid residues in murine TLR2, for example, murine TLR2 monomer (e.g. as shown in protein data bank (pdb) file 2Z81) or murine TLR2 heterodimer (e.g. as shown in pdb file 3A79), or a homologue thereof wherein said homologue comprises a binding site that has a root mean square deviation from the backbone atoms of said amino acid residues of between 0.00 Å and 2.50 Å and preferably between 0.00 Å and 2.00 Å, 0.00 Å and 1.50 Å, 0.00 Å and 1.00 Å or 0.00 Å and 0.50 Å. In certain embodiments, the structure coordinates are the same as structure coordinates of said amino acid residues in human TLR2, for example human TLR2 monomer (e.g. as shown in pdb file 2Z80) or human TLR2 heterodimer (e.g. as shown in pdb file 2Z7X), or a homologue thereof wherein said homologue comprises a binding site that has a root mean square deviation from the backbone atoms of said amino acid residues of between 0.00 Å and 2.50 Å and preferably between 0.00 Å and 2.00 Å, 0.00 Å and 1.50 Å, 0.00 Å and 1.00 Å or 0.00 Å and 0.50 Å.

Typically the binding epitope is defined by the structure coordinates of at least two, three, four, five, six, seven, eight or nine or all of amino acid residues His318, Pro320, Gln321 or Arg321, Tyr323, Lys347, Phe349, Leu371, Glu375, Tyr376 and His398.

This aspect of the invention further extends to an isolated nucleotide sequence encoding said fragment, a vector comprising said nucleotide sequence and a host comprising said vector.

According to a further aspect of the present invention there is provided a vaccine composition comprising the fragment of Toll-like receptor 2 (TLR2) of the invention.

The fragment of the present invention has utility in the provision of vaccine compositions which can be administered to subjects for use in the treatment of diseases which are mediated by TLR2 activation and/or signalling, e.g. chronic inflammatory conditions and chronic diseases. The host immune response will result in the production of antibodies which have binding specificity to the epitope of the invention. These antibodies will therefore function as TLR2 antagonistic antibodies.

According to a further aspect of the present invention there is provided a three-dimensional structure comprising a functional epitope wherein said epitope is defined by structure coordinates of one or more amino acid residues His318, Pro320, Gln321 or Arg321, Tyr323, Lys347, Phe349, Leu371, Glu375, Tyr376 and His398 of TLR2 and wherein said three-dimensional structure does not comprise the extracellular domain of TLR2.

Typically there is provided a three-dimensional structure comprising one or more of amino acid residues His, Pro, Gln or Arg, Tyr, Lys, Phe, Leu, Glu, Tyr and His wherein said one or more amino acid residues have the same structure coordinates as His318, Pro320, Gln321 or Arg321, Tyr323, Lys347, Phe349, Leu371, Glu375, Tyr376 and His398 in TLR2 and wherein said one or more amino acid residues form a functional epitope in said three-dimensional structure, wherein said three-dimensional structure does not comprise the extracellular domain of TLR2. The epitope is a functional epitope for receptor dimerization or inhibition thereof. Typically the epitope is bound by OPN-301 and OPN-305. Binding of the epitope by a binding member, such as an antibody, results in antagonism of TLR2 activation and signalling. In particular, binding by the binding member serves to inhibit activation of the TLR2 receptor, irrespective of whether a TLR2 heterodimer is formed with TLR1 or TLR6. Furthermore, antibodies binding to this epitope have been shown to cross-react with TLR2 from human, pig and monkey, indicating that this is a critical epitope in a highly conserved region of TLR2.

Typically the three-dimensional structure comprises at least two, three, four, five, six, seven, eight or nine or all of amino acid residues His318, Pro320, Gln321 or Arg321, Tyr323, Lys347, Phe349, Leu371, Glu375, Tyr376 and His398. Typically said at least two, three, four, five, six, seven, eight or nine or all amino acid residues His318, Pro320, Gln321 or Arg321, Tyr323, Lys347, Phe349, Leu371, Glu375, Tyr376 and His398 form the binding epitope. Other amino acid residues within the three-dimensional structure may also form part of the epitope.

The one or more amino acid residues may have the same structure coordinates as the identified amino acid residues in human or murine TLR2. Preferably, the structure coordinates of said one or more amino acid residues relate to when TLR2 is a monomer. In alternative embodiments, the structure coordinates relate to when TLR2 has formed a heterodimer. In certain embodiments, the structure coordinates are the structure coordinates of amino acid residues His318, Pro320, Gln321, Tyr323, Lys347, Phe349, Leu371, Glu75, Tyr376 and His398 of murine TLR2, for example, murine TLR2 monomer (e.g. as shown in pdb file 2Z81 as shown in FIG. 23) or murine TLR2 heterodimer (e.g. as shown in pdb file 3A79), or a homologue thereof wherein said homologue comprises a binding site that has a root mean square deviation from the backbone atoms of said amino acid residues of between 0.00 Å and 2.50 Å and preferably between 0.00 Å and 2.00 Å, 0.00 Å and 1.50 Å, 0.00 Å and 1.00 Å or 0.00 Å and 0.50 Å. In certain embodiments, the structure coordinates are the structure coordinates of amino acid residues His318, Pro320, Arg321, Tyr323, Lys347, Phe349, Leu371, Glu375, Tyr376 and His398 of human TLR2, for example human TLR2 monomer (e.g. as shown in pdb file 2Z80) or human TLR2 heterodimer (e.g. as shown in pdb file 2Z7X), or a homologue thereof wherein said homologue comprises a binding site that has a root mean square deviation from the backbone atoms of said amino acid residues of between 0.00 Å and 2.50 Å and preferably between 0.00 Å and 2.00 Å, 0.00 Å and 1.50 Å, 0.00 Å and 1.00 Å or 0.00 Å and 0.50 Å. In certain embodiments, the three-dimensional structure comprises one or more or all amino acid residues His, Pro, Gln, Tyr, Lys, Phe, Leu, Glu, Tyr and His (SEQ ID NO:2) optionally separated by one or more spacer amino acids. In certain embodiments, the three-dimensional structure comprises one or more or all amino acid residues His, Pro, Arg, Tyr, Lys, Phe, Leu, Glu, Tyr and His (SEQ ID NO:1) optionally separated by one or more spacer amino acids.

The three-dimensional structure is not TLR2 and does not comprise the extracellular domain of TLR2 or a C-terminal portion thereof. The term "extracellular domain" of TLR2 as used herein is understood to encompass fragments of TLR2 comprising amino acid residues 1-587, 1-570, 1-584, 221-587 and 292-586 of TLR2. The three-dimensional structure of the invention does not therefore comprise amino acid residues 1-587, 1-570, 1-584, 221-587 or 292-586 of TLR2.

Typically the three-dimensional structure is not a fragment of TLR2. Typically the three-dimensional structure has a non-TLR2 framework or scaffold to which the amino acid residues are attached to form the binding site or epitope. The scaffold provides the one or more amino acid residues with the same structure coordinates as His318, Pro320, Gln321 or Arg321, Tyr323, Lys347, Phe349, Leu371, Glu375, Tyr376 and His398 of TLR2. The term "non-TLR2" is understood to mean that at least part of the framework or scaffold is not derived or obtained from TLR2. The non-TLR2 component may be derived from a protein other than TLR2 or may be non-protein. Typically, the three-dimensional structure comprises a polypeptide comprising one or more or all of amino acid residues His, Pro, Gln or Arg Tyr, Lys, Phe, Leu, Glu, Tyr and His linked by spacer amino acids wherein the spacer amino acids are not derived from TLR2. Said spacer amino acids may serve to provide the three-dimensional structure with the same secondary structure as when these amino acid residues are present in TLR2. In particular, said spacer amino acids may serve to provide the amino acid residues His, Pro, Gln or Arg, Tyr, Lys, Phe, Leu, Glu, Tyr and His with the same structure coordinates as these amino acid residues have when present in TLR2. In certain embodiments, the three-dimensional structure has the form X-His318-X-Pro320-Arg321-X-Tyr323-X-X-      . . . X-Lys347-X-Phe349-X-X- . . . X-Leu371-X-X-X-Glu375-Tyr376-X-X- . . . X-His398-X, wherein X represents one or more spacer amino acid residues. In certain embodiments, the three-dimensional structure has the form X-His318-X-Pro320-Gln321-X-Tyr323-X-X- . . . X-Lys347-X-Phe349-X-X- . . . X-Leu371-X-X-X-Glu375-Tyr376-X-X- . . . X-His398-X, wherein X represents one or more spacer amino acid residues.

In certain embodiments, the three-dimensional structure comprises a fusion protein, for example, a fusion protein containing a leucine rich repeat protein, e.g. from Hagfish (variable lymphocyte receptors). Fusion proteins with leucine rich repeat proteins from Hagfish have been successfully used previously to study TLR2 function (Jin et al., Cell. 2007 Sep. 21; 130(6):1071-82). Such fusion proteins may be used as a framework to present the amino acid residues which form the epitope of the invention.

In certain embodiments the three-dimensional structure comprises at least some non-protein component. In certain embodiments the three-dimensional structure is synthetic or man made.

Typically the three-dimensional structure is an isolated or purified structure. Typically the three-dimensional structure comprises less than 500, 400, 300, 200, 100, 50, 30, 20, 15, 13, 12, 11 or 10 amino acids of TLR2. Typically the three-dimensional structure does not comprise a continuous stretch of more than 100, 90, 80, 70, 60, 50, 40, 30, 20, 10, 5, preferably more than 4, more preferably more than 3 and even more preferably more than 2 consecutive amino acids of TLR2. Typically the three-dimensional structure comprises, includes, consists essentially of or consists of amino acid residues 250 to 450, 300 to 400, 310 to 412, 310 to 411, 311 to 412, 311 to 411, 317 to 398 or 318 to 398 of TLR2, e.g. of human TLR2 as shown in SEQ ID NO:3 or murine TLR2 as shown in SEQ ID NO:4, or a sequence which has at least 80%, 85%, 90%, 95%, 96%, 97%, 98% or 99% amino acid sequence identity with said amino acid residues of TLR2. In certain embodiments the three-dimensional structure comprises the TLR2 fragment of the invention.

The three-dimensional structure provides a model of the TLR2 epitope and facilitates the generation or identification of binding members having binding specificity to the epitope. A template molecule may be selected as the three-dimensional structure onto which chemical groups which mimic the epitope are grafted having the specified structure coordinates. Binding members which target the epitope can be conveniently selected so that the binding member is easy to synthesise, is likely to be pharmacologically acceptable, and does not degrade in vivo, while retaining the biological activity of the binding member. Binding members identified by this approach can then be screened to see whether they bind to the identified TLR2 epitope and inhibit or reduce TLR2-mediated signalling. Further optimisation or modification can be carried out to arrive at one or more final binding members for in vivo or clinical testing.

According to a further aspect of the present invention there is provided a binding member which specifically binds to amino acid residues His318, Pro320, Tyr323, Lys347, Phe349, Leu371, Glu375, Tyr376 and His398 of TLR2 wherein the binding member is not T2.5 (OPN-301) or a humanised version thereof, e.g. the humanised version designated OPN-305 or the partially humanised version of T2.5 disclosed in WO 2005/028509.

In certain embodiments, the binding member further binds to amino acid residue Gln321 (murine) and/or Arg321 (human) of TLR2.

Typically the binding member specifically binds to the epitope of the TLR2 polypeptide fragment of the invention and/or the epitope of the three-dimensional structure of the invention.

Binding of the binding member to TLR2 results in antagonism of the function of TLR2, in particular antagonism of TLR2 activation and downstream mediated signalling. Typically binding serves to inhibit activation of the TLR2 receptor, irrespective of whether TLR2 forms a heterodimer with TLR1 or TLR6.

Typically the binding member binds to human TLR2 and/or murine TLR2. In certain embodiments the binding member binds TLR2 from any mammal, for example, a cow or rat. In certain embodiments the binding member is cross-reactive, that is, it has binding specificity for TLR2 derived from different species.

Typically the binding member binds to the ligand binding region of TLR2. Typically the binding member inhibits or prevents dimerization of TLR2 with TLR1 or TLR6 by covering the interaction surface between TLR2 and TLR1 or TLR6. Typically the binding region/interaction surface is located in LRR 11 to 14 of TLR2.

The binding member may be selected from the group consisting of a protein, a peptide, a peptidomimetic, a nucleic acid, a carbohydrate, a lipid, an oligopeptide, an aptamer and a small molecule compound. In certain embodiments the binding member is an antibody or an antibody binding fragment. The antibody is not the anti-TLR2 antibody designated TL2.1.

The binding member of the invention (e.g. antibody) has utility in methods and medicaments for the regulation or suppression of immune responses and in particular for the suppression of aberrant immune responses. The binding member (e.g. antibody) also has utility in the regulation of immune cell associated disorders, for example autoimmune diseases. In certain embodiments the binding member (e.g. antibody) can be used to deliver a therapeutic or cytotoxic agent to a TLR2 expressing cell. In certain embodiments the binding member (e.g. antibody) can be used diagnostically. Accordingly, the binding member provided in accordance with the present invention has utility in the diagnosis, treatment and prophylaxis of immune mediated conditions.

According to a further aspect of the present invention there is provided a method for the treatment or prophylaxis of a disease which is mediated by Toll-like Receptor 2 activation and/or signalling, the method comprising the step of administering to a subject in need of treatment a therapeutically effective amount of the binding member of the invention.

According to a further aspect of the present invention there is provided use of the binding member of the invention in the manufacture of a medicament for the treatment or prophylaxis of a disease which is mediated by Toll-like Receptor 2 activation and/or signalling.

According to a further aspect of the present invention there is provided the binding member of the invention for use as a medicament.

According to a further aspect of the present invention there is provided the binding member of the invention for use in the treatment or prophylaxis of a disease which is mediated by Toll-like Receptor 2 activation and/or signalling.

In certain embodiments, the disease which is mediated by Toll-like Receptor 2 activation and/or signalling is an immune-mediated condition.

According to a further aspect of the present invention there is provided a method for suppressing Toll-like receptor 2 (TLR2) functional activity, wherein said method comprises the steps of:
providing a therapeutically effective amount of the binding member of the invention; and
administering same to a subject in need thereof.

According to a further aspect of the present invention there is provided a pharmaceutical composition comprising the binding member of the invention and at least one pharmaceutically acceptable carrier, excipient or diluent.

In certain embodiments the pharmaceutical composition may further comprise a secondary therapeutic agent, such as a cytokine inhibitor or an immunosuppressant.

According to a further aspect of the present invention there is provided the use of the TLR2 polypeptide fragment of the invention or the three-dimensional structure of the invention in a method for generating a binding member which specifically binds to TLR2 and antagonises function of TLR2.

Typically the binding member antagonises TLR2 activation and downstream mediated signalling. Typically the binding member inhibits activation of TLR2, irrespective of whether TLR2 forms a heterodimer with TLR1 or TLR6. Typically the binding member specifically binds to the epitope of the invention.

According to a further aspect of the present invention there is provided the use of the TLR2 polypeptide fragment of the invention or the three-dimensional structure of the invention in a screening method or assay for identifying a binding member, for example a peptide, small molecule, aptamer or a chemical compound, which specifically binds to TLR2 and antagonises function of TLR2.

Typically the binding member antagonises TLR2 activation and downstream mediated signalling. Typically the binding member inhibits activation of TLR2, irrespective of whether TLR2 forms a heterodimer with TLR1 or TLR6. Typically the binding member specifically binds to the epitope of the invention.

In certain embodiments, the screening method for identifying an antagonist of TLR2 function comprises the steps of:
bringing a candidate compound into contact with the TLR2 polypeptide fragment of the invention or the three-dimensional structure of the invention; and
assessing binding between the candidate compound and the TLR2 polypeptide fragment of the invention or the three-dimensional structure of the invention;
wherein binding between the candidate compound and the TLR2 polypeptide fragment of the invention or the three-dimensional structure of the invention identifies the candidate compound as an antagonist of TLR2 function.

The method may optionally also include a step of contacting said candidate compound with TLR2 to determine the ability of the candidate compound to bind TLR2, and specifically to bind said amino acid residues. The method may optionally also include a step of assaying for inhibition of TLR2 functional activity by the candidate compound.

Typically the method is a method for identifying a compound having utility in the treatment of TLR2-mediated diseases or conditions. Binding of the compound to the TLR2 polypeptide fragment of the invention or the three-dimensional structure of the invention identifies the compound as having utility in the treatment of TLR2-mediated diseases or conditions.

The invention extends to binding members identified by said screening method.

A further aspect of the present invention provides an assay for assessing binding activity between the TLR2 polypeptide fragment of the invention or the three-dimensional structure of the invention and a candidate binding compound comprising the steps of:

bringing the candidate binding compound into contact with the TLR2 polypeptide fragment of the invention or the three-dimensional structure of the invention; and determining interaction or binding between the candidate binding compound and the TLR2 polypeptide fragment of the invention or the three-dimensional structure of the invention.

In the above aspects of the invention, binding may be determined by any number of techniques, both qualitative and quantitative which will be well known to the person skilled in the art.

The invention also provides a method of identifying a potential binding member or a binding member which specifically binds to TLR2 and antagonises function of TLR2. The method comprises the steps of:

using structure coordinates of TLR2 amino acid residues His318, Pro320, Gln321 or Arg321, Tyr323, Lys347, Phe349, Leu371, Glu375, Tyr376 and His398 to generate a three-dimensional structure comprising a binding epitope; and using said three-dimensional structure to design or select a potential binding member or a binding member having binding specificity to the binding epitope.

The method may optionally also include a step of contacting said potential binding member with TLR2 to determine the ability of the potential binding member to bind TLR2, and specifically to bind said amino acid residues. The method may optionally also include a step of assaying for inhibition of TLR2 functional activity by the binding member.

In certain embodiments the three-dimensional structure has one or more of the features of the three-dimensional structure of the invention as described above. In particular, in certain embodiments, the structure coordinates are structure coordinates of murine TLR2, for example as shown in pdb file 2Z81 as shown in FIG. 23 or a homologue thereof wherein said homologue comprises a binding site that has a root mean square deviation from the backbone atoms of said amino acid residues of between 0.00 Å and 2.50 Å and preferably between 0.00 Å and 2.00 Å, 0.00 Å and 1.50 Å, 0.00 Å and 1.00 Å or 0.00 Å and 0.50 Å. In certain embodiments, the structure coordinates are structure coordinates of human TLR2, for example as show in pdb file 2Z80 or a homologue thereof wherein said homologue comprises a binding site that has a root mean square deviation from the backbone atoms of said amino acid residues of between 0.00 Å and 2.50 Å and preferably between 0.00 Å and 2.00 Å, 0.00 Å and 1.50 Å, 0.00 Å and 1.00 Å or 0.00 Å and 0.50 Å.

According to a further aspect of the present invention there is provided a crystallisable composition comprising TLR2 complexed with a binding member that specifically binds to TLR2 and antagonises TLR2 activation and/or signalling.

Also provided is a crystal comprising TLR2 complexed with an antagonistic binding member, wherein said crystal effectively diffracts X-rays for the determination of atomic coordinates of the complex to a resolution of greater than 8 Å, preferably greater than 7 Å.

Typically the TLR2 comprises, consists essentially of or consists of amino acids 311 to 411, 317 to 398 or 318 to 398 of TLR2, for example TLR2 as shown in SEQ ID NO:3 (human TLR2) or SEQ ID NO:4 (murine TLR2). In certain embodiments the TLR2 comprises, consists essentially of or consists of amino acids 25 to 587 of TLR2, for example TLR2 as shown in SEQ ID NO:3 (human TLR2) or SEQ ID NO:4 (murine TLR2). In certain embodiments the TLR2 consists of amino acids 25 to 587 of SEQ ID NO:4 (murine TLR2).

Typically the binding member is an antibody or a binding fragment thereof, for example a Fab fragment. In certain embodiments the antibody is OPN-301 or OPN-305, or a binding fragment thereof, for example a Fab fragment. In certain embodiments the binding member is a Fab fragment of OPN-305.

In certain embodiments the TLR2 consists of amino acids 25 to 587 of SEQ ID NO:4 (murine TLR2) and the binding member is a Fab fragment of OPN-305.

Typically the crystal has a space group C222 and unit cell dimensions a=176 Å, b=310 Å and c=97 Å.

The invention further extends to methods for preparing and using such crystallisable compositions and crystals.

According to a further aspect of the present invention there is provided a method of identifying a mimetic of antibody OPN-305 comprising comparing a three-dimensional structure of a potential mimetic with a three dimensional structure determined for the crystal of the invention. Typically the three-dimensional structure of the potential mimetic is compared with at least the crystalline form of the binding member of the crystal of the invention. Typically structure coordinates of the three-dimensional structure of the potential mimetic are compared with the structure coordinates of at least one amino acid bound by OPN-305, as identified in SEQ ID NO:1 or SEQ ID NO:2, for example as provided in FIG. 23. Preferably the location of atoms of the potential mimetic that contact the TLR2 binding epitope correspond to the location of atoms of OPN-305 that contact the TLR2 binding epitope.

The method may optionally also include a step of contacting said potential mimetic with TLR2 to determine the ability of the potential mimetic to bind TLR2, and specifically to bind to the TLR2 epitope of the invention. The method may optionally also include a step of assaying physiological activity of the potential mimetic, e.g. by testing its ability to inhibit dimerization of TLR2 with TLR1 and/or TLR6.

As used herein, the terms "fragment of TLR2", "TLR2 fragment" or similar terms mean that the polypeptide fragment comprises less amino acids than TLR2. In particular, the polypeptide comprises less than 784 amino acids, this being the number of amino acids in full length TLR2 (e.g. human TLR2 as defined herein as SEQ ID NO:3 and murine TLR2 as defined herein as SEQ ID NO:4). References to a specific amino acid residue within TLR2 as provided herein are provided with reference to full length TLR2. It will be understood, for example, that amino acid residue His318 refers to a histidine residue which is present at position 318 of full length TLR2 (e.g. human TLR2 as defined herein as SEQ ID NO:3 or murine TLR2 as defined herein as SEQ ID NO:4). The position of said amino acid residue in the fragment will depend on the length of the fragment, for example, His318 may be present at position 2 of the fragment of the invention. Typically the fragment of TLR2 comprises less than 500, 400, 300, 200, 150, 140, 130, 125, 120, 110, 101, 100, 95, 90, 85, 84, 83, 82, 81 or 80 amino acids of TLR2. The term "fragment of Toll-like receptor 2 (TLR2)", "TLR2 fragment" or similar includes synthetic equivalents or mimetics of the TLR2 fragment of the invention. As such, in certain embodiments a mimetic of the TLR2 fragment is provided. The mimetic may have some or all of the amino acid residues which comprise the TLR2 fragment of the invention deleted or substituted.

As defined herein, the term "specifically binds", "binds specifically" or "binding specificity" refers to the ability of a binding member to bind to a specific target epitope (e.g. a specific target epitope on TLR2) with a greater affinity than its affinity for a non-target epitope (e.g. a different non-target epitope on TLR2). In certain embodiments the term refers to binding to a target epitope with an affinity which is at least 10, 50, 100, 250, 500 or 1000 times greater than its affinity for a non-target epitope. In certain embodiments binding affinity is determined by an affinity ELISA assay. In certain embodiments binding affinity is determined by a BIAcore assay. In certain embodiments binding affinity is determined by a kinetic method. In certain embodiments binding affinity is determined by an equilibrium/solution method. In certain embodiments the binding member of the invention binds to the epitope defined herein with high affinity, for example, with an affinity constant of at least about $10^7$ $M^{-1}$, typically about $10^8$ $M^{-1}$, and more typically, about $10^9$ $M^{-1}$ to $10^{10}$ $M^{-1}$ or stronger. In certain embodiments the binding member of the invention binds to the epitope defined herein with a $K_D$ of $4\times10^{-8}$ or $3\times10^{-8}$ or less. Typically the binding member modulates, e.g. reduces and/or inhibits, one or more TLR2 biological activities in a TLR2 responsive cell and/or tissue.

The term "epitope" or "binding site" as used herein relates to a portion, or portions, of a macromolecule which is capable of being bound by a specific binding member. Epitopes generally consist of chemically active surface groups and have specific three dimensional structural characteristics, as well as specific charge characteristics. The epitope identified herein is a "functional epitope" which is understood to mean that binding of a binding member to the epitope has an effect on the function of TLR2. In particular, binding of the epitope by a TLR2 binding member typically antagonises the biological activity of TLR2. The epitope is therefore known as an "inhibiting" epitope or an "inhibitory" epitope. An "inhibiting" or "inhibitory" epitope means an epitope present on TLR2 that when bound by a binding member, such as a small molecule or an antibody, results in loss or reduction of biological activity of TLR2.

Epitopes may be contiguous or non-contiguous sequences of amino acid residues comprised within a polypeptide sequence. The term "contiguous epitope" defines an epitope comprised of a linear series of amino acid residues within a polypeptide which define the epitope. A "non-contiguous epitope", which may also be referred to as a conformational or discontinuous epitope, is an epitope which is comprised of a series of amino acid residues which are non-linear in alignment, that is that the residues are spaced or grouped in a non-continuous manner along the length of a polypeptide sequence. A non-continuous epitope can be a discontinuous epitope wherein the amino acid residues are grouped into 2 linear sequences, or alternatively the non-continuous epitope can be a discontinuous scattered epitope wherein the residues which contribute to the epitope are provided in 3 or more groups of linear amino acid sequences arranged along the length of the polypeptide. The TLR2 binding epitope identified herein has been identified as a non-continuous epitope, and more specifically a discontinuous scattered epitope. The epitope is positioned at amino acid residues 318 to 398 of TLR2 as shown, for example, in SEQ ID NO:3 (human) or SEQ ID NO:4 (murine). More specifically the binding residues which contribute to said epitope are the amino acid residues shown in SEQ ID NO:1 (human) or SEQ ID NO:2 (murine).

The term "structure coordinates" refers to Cartesian atomic coordinates derived from mathematical equations related to the patterns obtained on diffraction of a monochromatic beam of X-rays by the atoms (scattering centres) of TLR2 in a crystal form. The diffraction data are used to calculate an electron density map of the repeating unit of the crystal. The electron density maps are then used to establish the individual atoms of the TLR2 binding epitope. It is understood that a set of structure coordinates for a polypeptide is a relative set of points that define a shape in three dimensions. Slight variations in the individual coordinates will have little effect on overall shape. For the purpose of the invention, any three-dimensional structure that has a root mean square deviation of conserved residue backbone atoms between 0.00 Å and 2.50 Å and preferably between 0.00 Å and 2.00 Å, 0.00 Å and 1.50 Å, 0.00 Å and 1.00 Å or 0.00 Å and 0.50 Å when superimposed on the relevant backbone atoms described by the structure coordinates of TLR2 (e.g. as listed in FIG. 23) are considered identical or the same. For the purpose of the invention, structure coordinates are considered identical or the same even if slight variations are present in the individual coordinates if these do not affect the overall shape defined by the structure coordinates. Protein data bank files can be accessed at the RCSB Protein Data Bank website.

By the term "Toll-like receptor 2 activation and downstream mediated signalling" it is meant any intracellular signalling which is induced by activated TLR2. The signalling may be a TLR2 specific pathway, or may be a "shared" pathway, wherein the pathway may be activated by other sources, for example, pathways which contribute to the activation of the transcription factor NF-kappaB.

The term "immune-mediated condition" as used herein refers to conditions which are mediated in part or in totality by Toll-like receptor 2-mediated immune cell activation. In certain embodiments the immune mediated condition is a disease or condition in which signalling mediated by Toll-like receptor 2 results in onset or progression of the disease or condition.

As used herein, the term "subject" or "patient" refers to an animal, preferably a mammal and in particular a human.

The term "consisting essentially of" as used herein means that the invention necessarily includes the listed items and is open to including unlisted items that do not materially affect the basic and novel properties of the invention, e.g. a fragment of the invention consisting essentially of specified amino acid residues which form the epitope of the invention may also include other amino acid residues which do not form part of the epitope.

Unless otherwise defined, all technical and scientific terms used herein have the meaning commonly understood by a person who is skilled in the art in the field of the present invention.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The nomenclature used to describe the polypeptide constituents of the present invention follows the conventional practice wherein the amino group (N) is presented to the left and the carboxyl group to the right of each amino acid residue.

The expression "amino acid" as used herein is intended to include both natural and synthetic amino acids, and both D and L amino acids. A synthetic amino acid also encompasses chemically modified amino acids, including, but not limited to salts, and amino acid derivatives such as amides. Amino acids present within the polypeptides of the present invention can be modified by methylation, amidation, acetylation or substitution with other chemical groups which can change the circulating half life without adversely affecting their biological activity.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived Furthermore the term "fusion protein" as used herein can also be taken to mean a fusion polypeptide, fusion peptide or the like, or may also be referred to as an immunoconjugate. The term "fusion protein" refers to a molecule in which two or more subunit molecules, typically polypeptides, are covalently or non-covalently linked.

As used herein, the term "therapeutically effective amount" means an amount which is required to reduce the severity of and/or ameliorate a TLR2-mediated disease or at least one symptom thereof.

As used herein, the term "prophylactically effective amount" relates to an amount which is required to prevent the initial onset, progression or recurrence of a TLR2-mediated disease or condition, or at least one symptom thereof in a subject.

As used herein, the term "treatment" and associated terms such as "treat" and "treating" means the reduction of the progression, severity and/or duration of a TLR2-mediated condition or at least one symptom thereof, wherein said reduction or amelioration results from the administration of a binding member which has specificity for the TLR2 binding epitope of the present invention. The term "treatment" therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition.

BRIEF DESCRIPTION OF THE FIGURES

The patent or application file contains at least one drawing executed in color. Copies of this patent or patent application publication with color drawing(s) will be provided upon request and payment of the necessary fee.

FIGS. 8A-8B show Fab heavy chain cleavage sites. (A) Calculation of molecular weights of the two possible Fab variants according to the measured masses during MS. (B) Amino acid sequence of Fab heavy chain (see SEQ ID NO: 9). The cleavage sites are indicated with the top arrows. The two disulfide bridges downstream of the cleavage sites are indicated with the lower arrows.

FIG. 19 shows an alignment of the dimerization site (human, mouse, monkey) and mutation analysis (sequences shown represent SEQ ID Nos.: 10-25).

FIG. 23 lists the atomic structure coordinates of the interaction site between murine TLR2 (PDB code 2Z81) and a Fab fragment of OPN-305 as derived by X-ray diffraction from crystals of murine TLR2/Fab fragment in protein data bank (PDB) format.

DETAILED DESCRIPTION OF THE INVENTION

Figure 1:
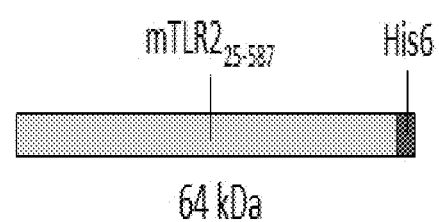
FIG. 1 shows a schematic representation of murine (m) TLR2$_{25-587}$-His. The extracellular domain (ECD) mTLR2$_{25-587}$ is C-terminal linked to a hexahistidin tag. The molecular weight of the recombinant protein is 64 kDa.

Having predicted the three dimensional structure of murine TLR2, the inventors have surprisingly identified a discontinuous, conformational binding epitope comprising amino acid resides present at amino acid residue numbers 318, 320, 321, 323, 347, 349, 371, 375, 376 and 398 of TLR2. All of these amino acids are exposed on the surface of the three dimensional structure towards OPN-305. The identified epitope spans the TLR2 ligand binding site and covers the interaction surface between TLR2 and TLR1 or TLR6. Without wishing to be bound by theory, the present inventors predict that binding to this epitope by a binding member, such as an antibody, causes the suppression and/or inhibition of the activation of TLR2 and/or of downstream signalling mediated by TLR2 irrespective of whether TLR2 forms a heterodimer with TLR1 or TLR6.

TLR2-Related Diseases

The detection of microbial and endogenous products by TLR2 and other TLRs induces the release of large amounts of inflammatory cytokines and chemokines, such as TNF-α, IL-1β and IL-6. Consequent hyperactivation of immune cells by bacteria through TLR2 stimulation can lead to septic shock pathology. Ulcerative colitis is associated with a R753G polymorphism of TLR2 and causes chronic intestinal inflammation. Likewise, the recognition of DAMPs released from inflamed tissues can lead to chronic inflammation, caused by a vicious cycle in which more inflammatory mediators are generated, leading to further activation of TLRs. TLR2- and TLR4-derived chronic inflammation can cause rheumatoid arthritis (RA) in synovial joints leading to destruction of cartilage and bone. TLR2 is also involved in the development of systemic lupus erythematosus and atherosclerosis. This can culminate in thrombosis and occlusion, resulting in a myocardial infarction or stroke. TLR2 is crucial in the development of ischemia/reperfusion (I/R) injury.

I/R injury is associated with trauma, stroke, myocardial infarction, and solid organ transplantation. The amount of brain damage and neurological deficits caused by a stroke were significantly less in mice deficient in TLR2 or -4 compared with wild type control mice. More recently, TLR2 has been implicated as a primary receptor for triggering neuroinflammatory activation through recognition of Alzheimer's amyloid β peptide.

Without being bound by theory, the inventors predict that inhibiting TLR2 function serves to suppress the expression of a number of cytokines and chemokines which are associated with the development and recurrence of cardiovascular disease. In certain specific embodiments the cytokine may be IL-1 beta. In certain embodiments the chemokine which is suppressed is MIP-1 alpha. In certain embodiments the present invention provides a method for the suppression of the expression or IL-1 beta and/or MIP-1 alpha. The disease or condition which is mediated by TLR2 activation and/or signalling therefore includes cardiovascular diseases, such as atherosclerosis. In certain embodiments the cardiovascular disease is selected from the group consisting of atherosclerosis, heart failure, myocarditis, myocardial dysfunction in sepsis, viral myocarditis and diabetes related angiopathy.

In certain embodiments binding to the identified epitope may result in the induction of regulatory T cell (Treg) activity. The activation of the Treg population of T cells results in the suppression of the immune response. As such, binding to the epitope of the present invention may result in the upregulation of Treg production.

The TLR2-mediated disease may be selected from the group consisting of immune-mediated conditions, inflammatory conditions, autoimmune conditions, pathogenic conditions and cancerous or malignant conditions, for example, septic shock, ulcerative colitis, chronic inflammation, rheumatoid arthritis, SLE, atherosclerosis, thrombosis, myocardial infarction and stroke.

In certain embodiments the pathogenic condition is an infectious condition mediated by bacteria. The bacteria may be gram positive bacteria, or alternatively gram negative bacteria. In certain embodiments the bacteria is a sepsis-causing bacteria, and as such the TLR2-mediated disease may be an endotoxin-mediated condition, for example sepsis, septic shock or septicaemia.

In certain embodiments the inflammatory condition is a cardiovascular disease, which may be selected from the group consisting of atherosclerosis, heart failure, cardiac inflammation, ischemia, reperfusion, myocarditis, myocardial dysfunction in sepsis, stoke viral myocarditis, vascular injury, for example injury which may result from angioplasty, stenting and bypass grafting and diabetes-related angiopathy. In certain embodiments the inflammatory condition is an autoimmune condition and may be selected from the group consisting of arthritis (including rheumatoid arthritis, juvenile rheumatoid arthritis, osteoarthritis, psoriatic arthritis), psoriasis, SLE, type I diabetes, type II diabetes, multiple sclerosis, allograft rejection, acute and chronic graft versus host disease, and tissue damage resulting from insult or injury. Further diseases include sepsis, including gram positive sepsis, cerebral malaria, gingivitis, diabetes mellitus, glomerular nephritis, myasthenia gravis, systemic lupus erythematosis, autoimmune thyroiditis, dermatitis (including atopic dermatitis and eczematous dermatitis), Sjogren's Syndrome, including keratoconjunctivitis sicca secondary to Sjogren's Syndrome, alopecia areata, allergic responses due to arthropod bite reactions, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anaemia, pure red cell anaemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, interstitial lung fibrosis, Alzheimer's disease, coeliac disease, colitis, asthma and atopic disease.

Antibodies

An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and a bi-specific antibody. In further embodiments, the antibody may be a camelid antibody, in particular a camelid heavy chain antibody. Further the antibody fragment may be a domain antibody or a nanobody derived from a camelid heavy chain antibody. In a further embodiment the antibody may be a shark antibody or a shark derived antibody.

As antibodies can be modified in a number of ways, the term "antibody" should be construed as covering any binding member or substance having a binding domain with the required specificity. The antibody of the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included.

Fragments of a whole antibody can perform the function of antigen binding. Examples of such binding fragments are; a Fab fragment comprising the VL, VH, CL and CH1 antibody domains; an Fv fragment consisting of the VL and VH domains of a single antibody; a F(ab')2 fragment, a bivalent fragment comprising two linked Fab fragments; a single chain Fv molecule (scFv), wherein a VH domain and a VL domain are linked by a peptide linker which allows the two domains to associate to form an antigen binding site; or a bi-specific antibody, which may be multivalent or multi-specific fragments constructed by gene fusion.

A fragment of an antibody for use in the present invention, for example, a fragment of a TLR2 specific antibody, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

A "derivative" of such an antibody or of a fragment of a TLR2 specific antibody means an antibody modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having TLR2 binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only. In certain embodiments, modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains: (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Such substituted residues also may be introduced into the conservative substitution sites or into the remaining (e.g., non-conserved) sites.

The term "antibody" includes antibodies which have been "humanised". Methods for making humanised antibodies are known in the art. A humanised antibody may be a modified antibody having the hypervariable region of a monoclonal antibody such as a TLR2 specific antibody and the constant region of a human antibody. Thus the binding member may comprise a human constant region.

The variable region other than the hypervariable region may also be derived from the variable region of a human antibody and/or may also be derived from a monoclonal antibody such as a TLR2 specific antibody. In such case, the entire variable region may be derived from murine monoclonal antibody a TLR2 specific antibody and the antibody is said to be chimerised. Methods for making chimerised antibodies are known in the art.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced.

In certain embodiments the antibody is selected from the group consisting of a human, humanised, chimeric, synthetic, camelid, shark and in-vitro antibody, or a binding fragment derived from any of same. In certain embodiments the antibody is an antibody binding fragment selected from the group consisting of a Fab, scFv, Fv and dAb fragment. In certain embodiments the antibody comprises two complete heavy chains and two complete light chains, or a binding fragment thereof. In certain embodiments the antibody is a monoclonal antibody. In certain embodiments the antibody is a polyclonal antibody. In certain embodiments the antibody has a dissociation constant (Kd) selected from the group consisting of: (i) a dissociation constant between $10^{-7}$ M and $10^{-11}$ M, (ii) a dissociation constant of between $10^{-8}$ M and $10^{-9}$ M, (iii) a dissociation constant of between $10^{-9}$ M and $10^{-10}$ M, (iv) a dissociation constant of between $10^{-11}$ M and $10^{-12}$ M. In certain embodiments the antibody is a heterotetrameric antibody.

The antibody of the invention may be a dimer formed between a complex of a heavy and light chains. The antibody can comprise at least one complete heavy chain and one complete light chain or can assume an alternative structure, for example, the antibody can be an antibody fragment which comprises only an antibody binding fragment, such as a Fab, F(ab')2, Fv or a single chain Fv (scFV). The antibody can be of an isotype selected from the group consisting of IgG, IgA, IgM and IgE. In particular, the antibody may be of the isotype IgG and may be of the subclass IgG1, IgG2, IgG3 or IgG4. In certain embodiments there is also provided an isolated nucleic acid or vector which encodes the variable domains of the heavy and/or light chains of the antibody.

An antibody as described herein may be linked to another functional molecule such as a polypeptide, for example, a Fab fragment.

In certain embodiments the antibodies provided by the invention can be used in methods for detecting the presence of Toll-like Receptor 2 in a sample in vitro. Typically, the sample is a biological sample and may be selected from the group consisting of serum, plasma, tissue and biopsy tissue. The antibodies of the invention also have utility in methods for in vivo detection of the presence of TLR2, for example using imaging techniques which will be well known to the person skilled in the field. In such instances, the imaging technique may involve the antibody being labelled directly or indirectly with a detectable substance to facilitate detection of bound or unbound antibody.

In certain embodiments the antibodies of the invention have utility in in vivo and in vitro methods for the delivery or targeting of a therapeutic agent to a TLR2 expressing cell.

Production of Antibodies

The antibodies or antibody fragments of and for use in the present invention may be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acids encoding them, by use of an expression system. Nucleic acids for use in accordance with the present invention may comprise DNA or RNA and may be wholly or partially synthetic. In a preferred aspect, nucleic acids for use in the invention codes for antibodies or antibody fragments of the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person using the information and references contained herein and techniques known in the art, given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NSO mouse myeloma cells. A common, preferred bacterial host is *E. coli*. The expression of antibodies and antibody fragments in prokaryotic cells such as *E. coli* is well established in the art. Expression in eukaryotic cells in culture is also available to those skilled in the art as an option for production of a binding member.

In preferred embodiments of the invention, recombinant nucleic acids comprising an insert coding for a heavy chain variable domain and/or for a light chain variable domain of antibodies are employed. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

Recombinant DNA technology may be used to improve the antibodies of the invention. Thus, chimeric antibodies may be constructed in order to decrease the immunogenicity thereof in diagnostic or therapeutic applications. Moreover, immunogenicity within, for example, a transgenic organism such as a pig, may be minimised, by altering the antibodies by CDR grafting in a technique analogous to humanising antibodies.

In order to reduce immunogenicity within a recipient, the invention may employ recombinant nucleic acids comprising an insert coding for a heavy chain variable domain of an antibody fused to a human constant domain. Likewise the invention concerns recombinant DNAs comprising an insert coding for a light chain variable domain of an antibody fused to a human constant domain kappa or lambda chain.

Antibodies may moreover be generated by mutagenesis of antibody genes to produce 5 artificial repertoires of antibodies. This technique allows the preparation of antibody libraries. Antibody libraries are also available commercially. Hence, the present invention advantageously employs artificial repertoires of immunoglobulins, preferably artificial scFv repertoires, as an immunoglobulin source in order to identify binding molecules which have specificity for the epitope of the present invention.

A combinatorial screening technique such as a phage display-based biopanning assay may be used to in order to identify binding members which have binding specificity to amino acid residues His318, Pro320, Tyr323, Lys347, Phe349, Leu371, Glu375, Tyr376 and His398 of TLR2, or the fragment or three-dimensional structure of the invention. Such phage display biopanning techniques involve the use of phage display libraries, which are utilised in methods which identify suitable binding members in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies.

In certain embodiments the antibody is a monoclonal antibody and may be produced using any suitable method which includes producing antibodies by continuous cell lines in culture. Suitable methods will be well known to the person skilled in the art. Chimeric antibodies or CDR-grafted antibodies are further provided within the scope of the present invention. In certain embodiments the antibodies of the invention may be produced by the expression of recombinant DNA in host cell. In certain embodiments humanized antibodies are also provided.

In certain embodiments the monoclonal antibodies may be human antibodies produced using transgenic animals, for example, transgenic mice, which have been genetically modified to delete or suppress the expression of endogenous murine immunoglobulin genes with loci encoding for human heavy and light chains being expressed in preference, this resulting in the production of fully human antibodies. In order to induce an immune response which results in the production of human antibodies in a transgenic mouse which expresses human immunoglobulin genes, an antigen comprising the TLR2 fragment or three-dimensional structure of the present invention may be administered to the mouse.

Antibody Selection Systems

Immunoglobulins which are able to bind to the epitope of the present invention and which accordingly may be used in the methods of the invention can be identified using any technique known to the skilled person. Such immunoglobulins may be conveniently isolated from libraries comprising artificial repertoires of immunoglobulin polypeptides. A "repertoire" refers to a set of molecules generated by random, semi-random or directed variation of one or more template molecules, at the nucleic acid level, in order to provide a multiplicity of binding specificities. Methods for generating repertoires are well characterised in the art.

Any library selection system may be used in conjunction with the invention.

Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in vitro selection and amplification of specific antibody fragments that bind a target antigen. The nucleotide sequences encoding the VH and VL regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward. Methods for the construction of bacteriophage antibody display libraries and lambda phage expression libraries are well known in the art.

An alternative to the use of phage or other cloned libraries is to use nucleic acid, preferably RNA, derived from the B cells of an animal which has been immunised with the selected target, e.g. the TLR2 epitope of the present invention.

Isolation of V-region and C-region mRNA permits antibody fragments, such as Fab or Fv, to be expressed intracellular. Briefly, RNA is isolated from the B cells of an immunised animal, for example from the spleen of an immunised mouse or the circulating B cells of a llama, and PCR primers used to amplify VH and VL cDNA selectively from the RNA pool. The VH and VL sequences thus obtained are joined to make scFv antibodies. PCR primer sequences may be based on published VH and VL sequences.

Other Binding Members

In certain embodiments the present invention extends to polypeptides which have affinity and binding specificity for the binding epitope of the present invention. Such polypeptides have utility in the regulation of the innate immune response and may be identified by a number of techniques which will be well known to the person skilled in the art. For example, combinatorial screening, such as phage display bio-panning, may be used to identify polypeptides which have binding specificity to the TLR2 binding epitope of the present invention.

In certain embodiments the binding member is provided as a soluble protein, for example as a fusion protein, such as an Fc fusion protein. In certain embodiments the fusion protein comprises the polypeptide defining the binding member conjoined to an Fc receptor binding polypeptide derived from an immunoglobulin, typically a human immunoglobulin. The polypeptide encoding the Fc receptor binding polypeptide may be obtained by recombinant methods or alternatively may be produced synthetically. In a further embodiment the Fc receptor binding polypeptide may be obtained following proteolytic digestion of immunoglobulin molecules, for example by papain digestion of immunoglobulins. The binding member polypeptide may be coupled to the Fc receptor binding polypeptide by any method known in the art including chemical linkages. For example, the conjugation can involve the use of chemical crosslinking molecules, such as the use of heterobifunctional crosslinking agents, such as succinimidyl esters, for example, 3-(2-pyridyldithio)propionate or succinimidyl acetylthioacetate.

The polypeptide defining the binding member of the invention, or a fragment thereof, may be modified to create derivatives by forming covalent or aggregative conjugates with other chemical moieties, such as glycosyl groups, polyethylene glycol (PEG) groups, lipids, phosphate, acetyl groups and the like. Covalent derivatives of the polypeptides of the invention can be prepared by linking the chemical moieties to functional groups on the amino acid side chains or at the N-terminus or C-terminus of the polypeptide.

Mimetics

Peptide analogues, such as peptidomimetics or peptide mimetics are non-peptide compounds with properties representative of a template peptide. Such peptide analogues are typically developed using computerised molecular modelling. Peptidomimetics which are structurally similar to peptides which have affinity and binding specificity to the TLR2 binding epitope of the present invention may be used to mediate similar diagnostic, prophylactic and therapeutic effects.

Peptidomimetics are typically structurally similar to a template peptide, but have one or more peptide linkages replaced by an alternative linkage, by methods which are well known in the art. For example, a peptide which has a binding specificity for the TLR2 epitope of the invention may be modified such that it comprises amide bond replacement, incorporation of non peptide moieties, or backbone cyclisation. Suitably if cysteine is present the thiol of this residue is capped to prevent damage of the free sulphate group. A peptide may further be modified from the natural sequence to protect the peptides from protease attack.

Suitably a peptide of and for use in the present invention may be further modified using at least one of C and/or N-terminal capping, and/or cysteine residue capping. Suitably, a peptide of and for use in the present invention may be capped at the N terminal residue with an acetyl group. Suitably, a peptide of and for use in the present invention may be capped at the C terminal with an amide group. Suitably, the thiol groups of cysteines are capped with acetamido methyl groups.

In certain embodiments the binding member may be a mimetic or mimic. The designing of mimetics to a known pharmaceutically active compound is a known approach in the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property. There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore". Once the pharmacophore has been determined, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can also be used in this modelling process.

Purification/Production of Polypeptides

Expression, isolation and purification of polypeptides defining the epitope of the invention and fragments thereof may be accomplished by any suitable technique.

A method for producing polypeptides comprises culturing host cells transformed with a recombinant expression vector encoding a polypeptide having the amino acid sequence of the TLR2 fragment of the invention, for example SEQ ID NO:5 or SEQ ID NO:6 or a sequence which has at least 80% amino acid sequence identity thereto under conditions that promote expression of the polypeptide, then recovering the expressed polypeptides from the culture. The skilled man will recognise that the procedure for purifying the expressed polypeptides will vary according to such factors as the type of host cell employed, and whether the polypeptide is intracellular, membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired (*E. coli*) host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide during translation, but allows secretion of polypeptide from the cell.

Suitable host cells for expression of polypeptides include higher eukaryotic cells and yeast. Prokaryotic systems are also suitable. Mammalian cells, and in particular CHO cells are particularly preferred for use as host cells.

Candidate Compounds

The present invention provides assay methods for identifying compounds which exhibit binding affinity to the TLR2 epitope of the present invention. The interaction of such molecules with the binding epitope of the present invention may be useful in a therapeutic and prophylactic context.

It is well known that pharmaceutical research leading to the identification of a new drug may involve the screening of a very large number of candidate substances, both before and even after a lead compound has been found. Such means for screening for compounds which have binding affinity for the epitope of the present invention are further provided by the present invention. Compounds identified as binding compounds of the epitope of the present invention represent an advance in the therapy in these areas as they provide basis for design and investigation of therapeutics for in vivo use.

In various further aspects, the present invention relates to screening and assay methods and to compounds identified thereby, wherein said binding compounds have affinity and binding specificity for the epitope of the invention.

In certain embodiments the candidate binding compound is selected from the group consisting of a peptide, for example an antibody or antibody fragment, a chemical compound and a peptidomimetic. In certain embodiments the candidate binding compound is a natural or synthetic chemical compound used in a drug screening programmes. Extracts of plants which contain several characterised or uncharacterised components may be used.

A candidate binding compound which has affinity and binding specificity for the binding epitope of the present invention may be isolated and/or purified, manufactured and/or used to modulate TLR2 functional activity.

The precise format of the candidate binding compound screening assays of this aspect of the invention may be varied by those skilled in the art using routine skill and knowledge.

The invention extends to the use of combinatorial library technology which provides an efficient way of testing a potentially vast number of different substances for ability their ability to bind to an epitope or to modulate the activity of a binding compound which binds to an epitope. Prior to or as well as being screened for modulation of activity, candidate binding compounds may be screened for the ability to interact with the polypeptide, e.g. in a yeast two-hybrid system (which requires that both the polypeptide and the candidate binding compound can be expressed in yeast from encoding nucleic acid). This may be used as a coarse screen prior to testing a substance for actual ability to modulate activity of the polypeptide.

The amount of candidate binding compound which may be added to an assay of the invention will normally be determined by trial and error depending upon the type of compound used. Typically, from about 0.01 to 100 nM concentrations of the candidate binding compound may be used, for example from 0.1 to 10 nM. Greater concentrations may be used when the candidate binding compound is a peptide.

Sequence Homology

The present invention extends to sequences having at least 80% amino acid sequence identity to the TLR2 fragments of the invention. Such sequences or polypeptides may comprise a sequence which is substantially homologous to a polypeptide having the amino acid sequence of SEQ ID NO:5 or SEQ ID NO:6, but have an amino acid sequence different from that of SEQ ID NO:5 or SEQ ID NO:6 because of one or more deletions, insertions, or substitutions. The substantially homologous polypeptide may have an amino acid sequence that preferably is at least 80% identical to SEQ ID NO:5 or SEQ ID NO:6, and more preferably at least 90% identical. The substantially homologous polypeptide may include 1, 2 or more amino acid alterations. Alternatively, or in addition, the substantially homologous polypeptide may consist of a truncated version of the polypeptide of SEQ ID NO:5 or SEQ ID NO:6 which has been truncated by 1, 2 or more amino acids.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the nucleic acids of the invention include variants that differ from a native DNA sequence because of one or more deletions, insertions or substitutions, but that encode a biologically active polypeptide.

As used herein, percent amino acid sequence identity may be determined, using any method known to the person skilled in the art, for example, by comparing sequence information using the GAP computer program, version 6.0 described by Devereux et al. (Nucl. Acids Res. 12:387, 1984) and available from the University of Wisconsin Genetics Computer Group (UWGCG).

Crystal Structures

The invention extends to crystals of the crystallisable compositions of the present invention. The invention provides a three-dimensional structure obtained by X-ray crystallography of a TLR2/TLR2 binding member complex at high resolution. The three-dimensional structures of other crystallisable compositions of the invention may also be determined by X-ray crystallography.

Administration

The binding member of the present invention may be administered alone but will preferably be administered as a pharmaceutical composition, which will generally comprise a suitable pharmaceutically acceptable excipient, diluent or carrier selected depending on the intended route of administration. Examples of suitable pharmaceutical carriers include; water, glycerol, ethanol and the like.

The binding member of the present invention may be administered to a patient in need of treatment via any suitable route. As detailed herein, it is preferred that the composition is administered parenterally by injection or infusion. Examples of preferred routes for parenteral administration include intravenous, intracardial, intraarterial, intraperitoneal, intramuscular, intracavity, subcutaneous, transmucosal, inhalation and transdermal.

Routes of administration may further include topical and enteral, for example, mucosal (including pulmonary), oral, nasal, rectal.

In certain embodiments the composition is deliverable as an injectable composition. For intravenous, intradermal or subcutaneous application, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

The composition is preferably administered to an individual in a "therapeutically effective amount", this being sufficient to show benefit to the individual to whom the composition is administered. The actual dose administered, and rate and time-course of administration, will depend on, and can be determined with due reference to, the nature and severity of the condition which is being treated, as well as factors such as the age, sex and weight of the patient to be treated and the route of administration. Further due consideration should be given to the properties of the composition, for example, its binding activity and in vivo plasma life, the concentration of the fusion protein in the formulation, as well as the route, site and rate of delivery.

Dosage regimens can include a single administration of the composition of the invention, or multiple administrative doses of the composition. The compositions can further be administered sequentially or separately with other therapeutics and medicaments which are used for the treatment of the condition for which the fusion protein of the present invention is being administered to treat.

Examples of dosage regimens which can be administered to a subject can be selected from the group comprising, but not limited to; 1 µg/kg/day through to 20 mg/kg/day, 1 µg/kg/day through to 10 mg/kg/day, 10 µg/kg/day through to 1 mg/kg/day.

The present invention will now be described with reference to the following examples which are provided for the purpose of illustration and are not intended to be construed as being limiting on the present invention.

EXAMPLES

Example 1—Inhibition of mTLR2 with OPN-305 and Analysis of the Epitope

The present inventors have utilised structural methods such as crystallography and electron microscopy to solve the structure of the TLR2-OPN-305 complex and to explain how TLR2 silencing by OPN-305 is achieved. For that purpose protocols for the purification of TLR2 and antibody as well as for the purification of the TLR2-Fab complex had to be established in order to obtain protein in amounts and purity suitable for crystallization and EM trials. Prior to antibody purification, antibody Fab fragments had to be generated by proteolytic cleavage. The crystallization conditions had to be modulated to improve crystal growth and quality. Furthermore, as TLR2 is a glycoprotein, the impact of glycosylation on crystallization had to be analyzed. In case of a successful solution of the TLR2-Fab structure, functional studies had to be performed to unravel the mechanism of TLR2 inhibition by OPN-305. The solved structure had to be compared with other TLR2 complex structures and literature had to be consulted in order to analyse the structure.

Methods

Expression and Purification of mTLR2

The extracellular domain of mTLR2 (a. a. 1-587) was recombinantly expressed with a C-terminal linked hexahistidin tag in Sf21 insect cells in a 6 L scale, and in CHO lec3.2.8.1 cells (Stanley 1989; Wilke et al. 2010) in a 35 L scale (Dr. Joop van den Heuvel, HZI, Braunschweig Germany). The native N-terminal signal peptide (a. a. 1-24) which led to the secretion of the protein into the medium was cleaved by the cell own signal peptidase during translocation of the protein through the cell membrane. After 72 hours the cells were removed by centrifugation and the supernatant was then filtered, concentrated (Sf21 cells: 10×, CHO cells: 20×) and dialyzed against 50 mM Tris pH 8, 500 mM NaCl, and 5% glycerole. 0.1% sodium azide was added to prevent bacterial and fungal growth. The shipment to South Africa was done at 4° C. and took 3-4 days. Prior to purification a "Complete" protease inhibitor cocktail tablet, EDTA-free (Roche) was added to the protein solution and the sample centrifuged for 1 h at 16'500 rpm (Centrifuge RC6, Sorvall). Initial purification was achieved by Ni-NTA chromatography (Qiagen). The protein was immobilized and the column was washed with ~400 mL wash-buffer 1 (50 mM Tris pH 8, 300 mM NaCl, 10 mM imidazole) and ~75 mL wash-buffer 2 (50 mM Tris pH 8, 300 mM NaCl, 40 mM imidazole). $mTLR2_{25-587}$ was eluted by stepwise addition of elution buffer (50 mM Tris pH 8, 50 mM NaCl; imidazole steps: 100, 250, 500 mM). After elution, $mTLR2_{25-587}$ was diluted with 25 mM Tris pH8, 25 mM NaCl to reach an imidazole concentration below 50 mM. The protein was then further purified by anion exchange chromatography (MonoQ HR10/10, GE Healthcare). The protein was eluted using a salt gradient running from 80 to 200 mM during 25 column volumes. The pure protein (purity>95%) was concentrated to 2 mg/mL. For deglycosylation, 10 units of PNGase F (NEB) were utilized per 10 µg of $mTLR2_{25-587}$ and incubated for 15 h at room temperature in 50 mM Tris pH 8, 50 mM NaCl. The protein was either immediately used for complex formation or shock frozen in liquid nitrogen and stored at −80° C.

Papain Digestion and Purification of OPN-305

The antibody OPN-305 was provided by Opsona Therapeutics (Dublin, Ireland) in 10 mg/mL stocks in 25 mM sodium citrate pH 4.5 and 125 mM NaCl. The antibody was shock frozen in liquid $N_2$ and stored at −80° C. until usage. For papain cleavage of the antibody, the enzyme (Roche) was first activated by incubating in 100 mM Tris pH 8, 20 mM L-Cysteine for 30 min at 37° C., and the antibody buffer was exchanged by adding 100 mM Tris pH 8. Cleavage was initiated by mixing activated papain and antibody (mass ratio 1:20) and incubation for at least 8 h at 37° C. Size exclusion chromatography (Superdex 200 16/60, GE Healthcare) with 50 mM Tris pH 8, 50 mM NaCl running buffer was performed to separate the fully cleaved antibody from incomplete cleaved molecules. Incomplete cleaved antibody was pooled and used within the next digestion. OPN-305 Fab fractions were concentrated and further purified performing a second run of size exclusion chromatography. OPN-305 Fab was stored at −80° C. after shock freezing in liquid nitrogen.

Mass Spectrometry

For electrospray ionization mass spectrometry (ESI-MS) of OPN-305 Fab, the sample buffer was desalted and exchanged to 10 mM ammonium acetate pH 5 using a PD-10 column (GE Healthcare). The sample was concentrated to 10.8 mg/mL (220 µM). Mass spectrometry was performed by Central Analytical Facilities (University of Stellenbosch, Bellville, South Africa).

Purification of the mTLR2$_{25\text{-}587}$/Fab Complex mTLR2$_{25\text{-}587}$ and OPN-305 Fab were mixed in a molar ratio of 1:20 and subjected to size exclusion chromatography (Superdex 200 16/60, GE Healthcare) using 25 mM Tris pH 8, 25 mM NaCl as running buffer. The complex fractions were diluted to 12 mM Tris pH 8, 12 mM NaCl with water and concentrated to 20 mg/mL prior to crystallization setups.

Native PAGE

The native PAGE was performed according to standard SDS-PAGE (Laemmli 1970), but no SDS and reducing agent were used in the electrophoresis solutions and the gel. The run was done on ice using a low voltage of 100 V to avoid overheating of the gel and thus denaturing of the proteins.

Modeling of OPN-305

The OPN-305 Fab heavy chain and light chain were modelled by 3D structure prediction using SWISS-Model (Arnold et al. 2006; Kiefer et al. 2009; Peitsch et al. 1995). Then, the modelled structure was aligned with the crystal structure of b12 (pdb entry: 2NY7; (Zhou et al. 2007)), an antibody Fab fragment with identical constant domain sequence to OPN-305, in UCSF Chimera (Pettersen et al. 2004). Using b12 as a framework, the variable domain of b12 was replaced by the modelled OPN-305 variable domain.

Specimen Preparation and EM of mTLR2$_{25\text{-}587}$/Fab

A sample of mTLR2$_{25\text{-}587}$/Fab in 25 mM Tris pH 8, 25 mM NaCl was diluted to 39 nM and stained with 2% uranyl acetate (wt/vol). Staining and grid preparation were done as previously described (Ohi et al. 2004). The images were collected on a LEO 912 electron microscope (Leo Electron) operated at an acceleration voltage of 125 kV under low-dose conditions at a magnification of ×48'000 and a defocus value between 0.5 and 1.0 µm.

Referenced-Based Single-Particle Reconstruction

The images were converted to mrc format and 5174 individual particles were selected using the program sparx (Hohn et al. 2007). Mathematical image analysis were carried out with the software SPIDER (Frank et al. 1981; Frank et al. 1996). The particles were binned by a factor of 2 resulting in 64×64 pixel images with 4.48 Å/pixel. The particle stack was reference-free aligned by rotation and translation operations and the images were grouped into 50 classes by K-means classification (Penczek et al. 1992). Because no 3D reference was available for mTLR2$_{25\text{-}587}$/Fab, the high quality class averages with sharp particle boundary and flat background were used for 3D modelling of the mTLR2$_{25\text{-}587}$/Fab complex in PyMOL (Schrödinger, USA) by fitting the crystal structures of mTLR2 (PDB entry: 2Z82) (Jin et al. 2007) and the 3D model of OPN-305 (0) according to the particle shape seen in the averages. The resolution of the model was truncated to 30 Å and used as a first reference for single-particle reconstruction using the reference-based alignment method in SPIDER (Shaikh et al. 2008a). In total 86 2D reference projections were created from the 3D reference, and the obtained alignment parameters (shifts and rotations) were applied on the particle stack by alignment of the particles against the 2D references. An initial 3D reconstruction was computed from the aligned particle images. 39 iterations of back-projections and angular refinement were performed in SPIDER to improve the density map. The aligned particles of a given reference view were displayed to control the distribution of particles among projections. The 3D reconstruction resolution was calculated by splitting the particle data into two equal sets prior to the back-projection procedure and comparison of the two resulting half-reconstructions. Using the Fourier shell correlation (FSC)=0.5 criteria (Shaikh et al. 2008b), a resolution of 21.7 Å was calculated from the FSC curve of the final density map. Density map visualization, docking of the crystal structures and image preparation were performed using the Chimera software (Goddard et al. 2007; Pettersen et al. 2004).

Crystallization of mTLR2$_{25\text{-}587}$/Fab

Initial crystallization setups were carried out using the Mosquito 4B nanoliter pipeting robot (TTP LabTech, UK). mTLR2$_{25\text{-}587}$/Fab needle cluster crystals were grown after 3 weeks at 16° C. by sitting-drop vapour-diffusion using equal volumes (200 nL) of protein (20 mg/mL) and reservoir solution (100 mM MES pH 6, 100 mM MgCl$_2$, 8% PEG 6000) and cross-seeding with Internalin C crystals (50 nL seed stock). Extensive optimization of crystallization conditions including temperature screening, additive screening and variation of protein/reservoir ratio were performed. Single crystals were produced by micro-seeding at 16° C. using 2 µL of protein (11 mg/mL) and 2 µL of reservoir solution containing 100 mM MES pH 6, 120 mM MgCl$_2$, 10% PEG 6000, 3% glycerole in sitting-drop vapor-diffusion setups. Crystals grew after 2 month in the space group C222 with unit cell dimensions of a=176 Å, b=310 Å, and c=97 Å and diffracted up to 7 Å.

Data Collection and Evaluation

X-ray diffraction data set for mTLR2$_{25\text{-}587}$/Fab was collected at λ=1.54 Å on a home source rotating anode (MicroMax-007HF Generator; Rigaku, Tokyo, Japan) using a Saturn 944HG CCD detector (Rigaku, Tokyo, Japan). HKL3000 beta (Minor et al. 2006; Otwinowski and Minor 1997) and the CCP4 software suite (Collaborative Computational Project Number 4 1994) were used for data processing. A solvent content of 57% were obtained by assuming two complex molecules/asymmetric unit (Kantardjieff and Rupp 2003; Matthews 1968). Molecular replacement trials were done with PHASER (McCoy et al. 2007) and MOLREP (Vagin and Teplyakov 2010).

Results

Antibody

The antibody used in these studies, the monoclonal anti-human/mouse TLR2 antibody OPN-305 (Opsona Therapeutics, Dublin, Ireland) is a humanized version of the murine anti-human/mouse TLR2 antibody OPN-301, first developed by Prof. Dr. Carsten Kirschning (Universitätsklinikum Essen, Germany) as antibody T2.5. OPN-305 was provided by Opsona in 10 mg/mL stocks in 25 mM sodium citrate pH 4.5 and 125 mM NaCl. The antibody was shock frozen in liquid N$_2$ and stored at −80° C. until usage.

The mTLR2 clone was initially isolated by Prof. Dr. Carsten Kirschning for expression of mTLR2 in HEK293 cells (Meng et al. 2004), and later recloned into a pFastbac vector by Ute Widow (HZI, Braunschweig, Germany) for the expression in insect cells. A Histidin tag was further added to the C-terminus. The protein production was performed by the group of Dr. Joop van den Heuvel (HZI, Braunschweig Germany) and shipped on ice to South Africa. Until June 2011 the protein was produced in 6 L Sf21 insect cell cultures, the last production was performed as a 35 L fermenter in CHO lec3.2.8.1 cells, optimized for the production of proteins for structural analysis.

Purification of mTLR2

For simplification, the histidin-tagged ECD of murine TLR2, $mTLR2_{25-587}$-His, is termed as TLR2 from here on. The C-terminal histidin tag linked to TLR2 allows the usage of Ni-NTA affinity chromatography (AC) as first purification step, following anion exchange chromatography. TLR2 from insect cells and CHO cells showed the same behaviour in all chromatographic purification steps. The quality of the purification was analyzed by SDS-PAGE (FIG. 2).

Figure 2:
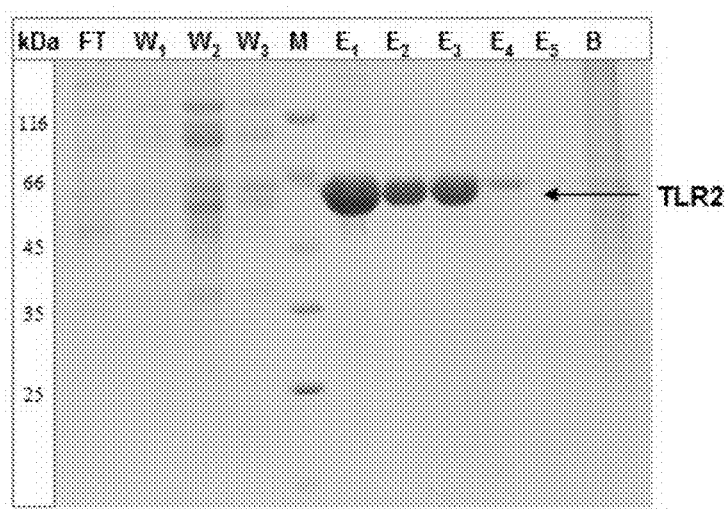
FIG. 2 shows purification of TLR2 by Ni-NTA affinity chromatography. SDS-PAGE of samples of the flow through (FT); the wash fractions $W_1$ (10 mM imidazole), $W_2+W_3$ (40 mM imidazole); the elution fractions $E_1+E_2$ (100 mM imidazole), $E_3+E_4$ (250 mM imidazole), $E_5$ (500 mM imidazole), and the beads after elution (B). TLR2 eluted with buffers containing 100 mM and 250 mM imidazole. Gel marker: Unstained Protein Molecular Weight Marker (Fermentas).

After coupling of the protein to the Ni-NTA matrix, the relative amount of impurities could be significantly lowered by washing with buffers containing 10 mM and 40 mM imidazole (FIG. 2, lanes $W_1$-$W_3$). TLR2 was eluted with 100 mM to 500 mM imidazole concentration (FIG. 2, lanes $E_1$-$E_5$), only small amounts remained on the beads (FIG. 2, lane B). The usual yield after this step was 0.4-0.5 mg protein per L insect cell culture and 0.6 mg protein per L CHO cell culture.

Figure 3:
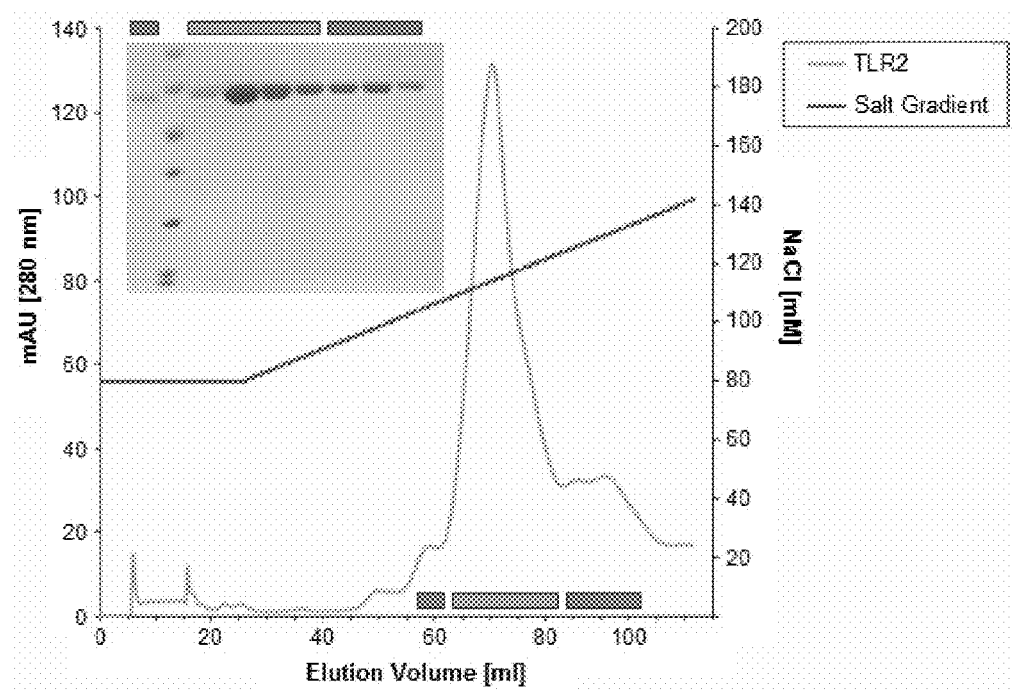
FIG. 3 shows purification of TLR2 by anion exchange chromatography. The target protein fractions from the AC were separated by AEC. The proteins were eluted from the column dependent by their negative charge by applying a salt gradient from 8 mM to 200 mM NaCl (straight line) and were monitored by measuring the absorption at 280 nm (curve). The elution fractions were analyzed by SDS-PAGE. Fractions from the main peak marked with a centre bar were used for the complexation with the antibody. Gel marker: Unstained Protein Molecular Weight Marker (Fermentas).

To further separate the remaining impurities (FIG. 2, lane $E_1$) from the target protein, an anion exchange chromatography (AEC) was performed (FIG. 3). By applying a salt gradient to the AEC column, protein eluted with buffer containing 100 mM to 140 mM NaCl, with a maximum at 115 mM NaCl (FIG. 3), detected as one major and several smaller peaks of absorbance at 280 nm. The corresponding elution fractions were analyzed by SDS-PAGE by which all samples were identified as TLR2. No more impurities were detectable. The different peaks may be the result of different glycosylation states of TLR2, that's why only the central fractions of the main peak (FIG. 3, middle bar) were pooled and used for further experiments.

Deglycosylation of TLR2

Figure 4:
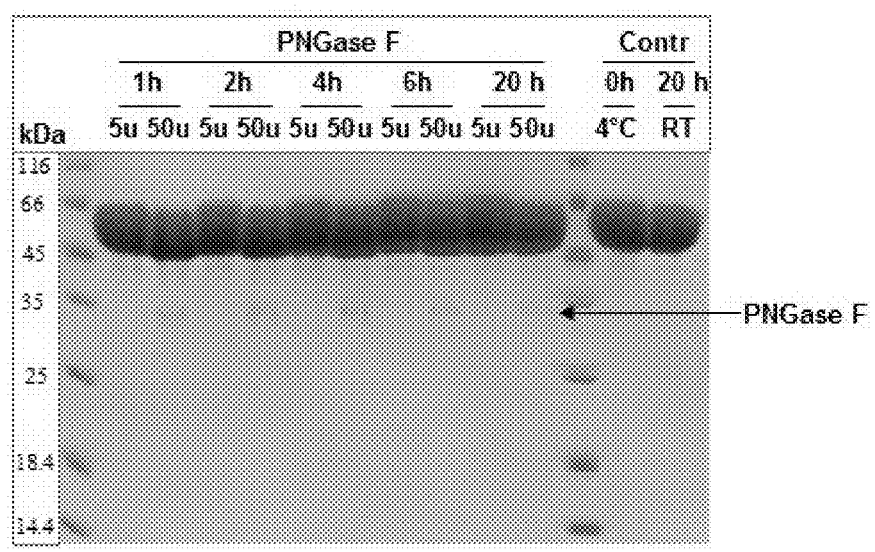
FIG. 4 shows deglycosylation of TLR2. 11 μg of TLR2 were incubated with 5 u and 50 u PNGase F for 1 hour (h), 2 h, 4 h, 6 h, and 20 h at room temperature (RT). The reaction was stopped by adding SDS buffer and denaturation of the samples at 95° C. The samples were analyzed by SDS-PAGE. Controls without enzyme were analyzed before start (0 h) at 4° C. and after 20 hours at RT. Gel marker: Unstained Protein Molecular Weight Marker (Fermentas).

The ECD of mTLR2 exhibits three glycosylation sides. Although the protein expression systems in Sf21 insect cells and especially in the used CHO strain already perform an optimized glycosylation with shorter and more homogeneous sugar chains, glycosylation in general and glycosylation variability in particular can still lead to additional challenges during crystallization. Deglycosylation of TLR2 was performed with PNGase F, an amidase that cleaves between the innermost GlcNAc and asparagine residues from N-linked glycoproteins. The SDS gel shown in FIG. 4 shows TLR2 cleavage with two enzyme concentrations and different incubation times.

Using 50 u PNGase F, 11 µg of protein was fully cleaved after 1 hour incubation. Between 6 hours and 20 hours were necessary to deglycosylate the protein using 5 u PNGase F. TLR2 shows no denaturation after 20 hours at room temperature (RT). Deglycosylation of TLR2 was tested from insect cells as well from CHO cells, but only deglycosylation of TLR2 from insect cells could be observed by SDS-PAGE, indicating that the glycosylation state of proteins produced in CHO cells is already too low for being able to see a mass difference by SDS-PAGE after cleavage. No differences during AEC could be observed between deglycosylated and glycosylated TLR2. According to the results in FIG. 4, 10 u of PNGase F were used per 10 µg of protein during an incubation of 15 hours at RT in further deglycosylation experiments.

Glycosylated as well as deglycosylated TLR2 were used for complex formation and following crystallization studies.

Generation and Purification of Antibody Fab Fragments

Figure 5:
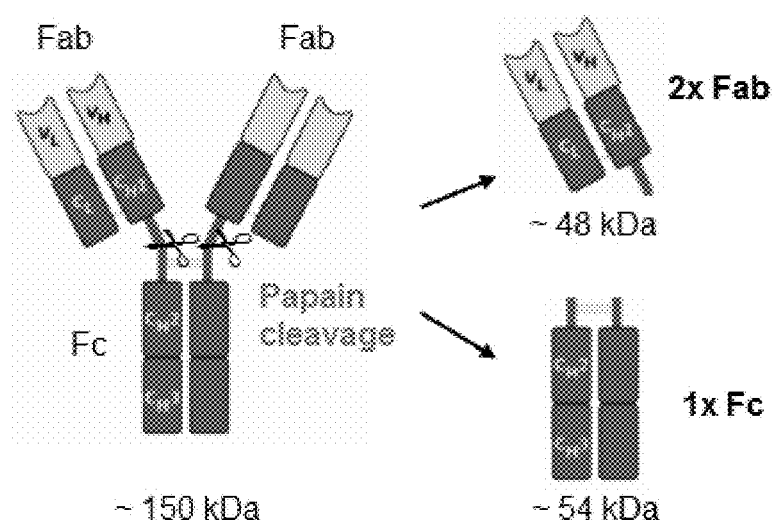
FIG. 5 shows papain cleavage of antibodies. Antibody OPN-305 has two papain cleavage sites, one on each heavy chain (scissor symbols). Digestion results in two Fab fragments (~48 kDa each) and one Fc fragment (~54 kDa).

The two heavy and two light chains of an antibody form three domains, two identical Fab domains and one Fc domain. Because only the Fab fragments contain the variable regions with the CDRs which are responsible for antigen recognition, the antibody OPN-305 was digested with the enzyme papain, a cysteine protease which cleaves antibodies above the two central disulfide bridges of the heavy chain resulting in two single Fab domains and one Fc domain (FIG. 5). Using the smaller Fab fragments for structural studies instead of using the full length antibody is preferred, because an uncleaved antibody can bind two TLR molecules and moreover is very flexible at the joint of the three domains, which may constitute major obstacles for subsequent crystallization and EM.

Figure 6:
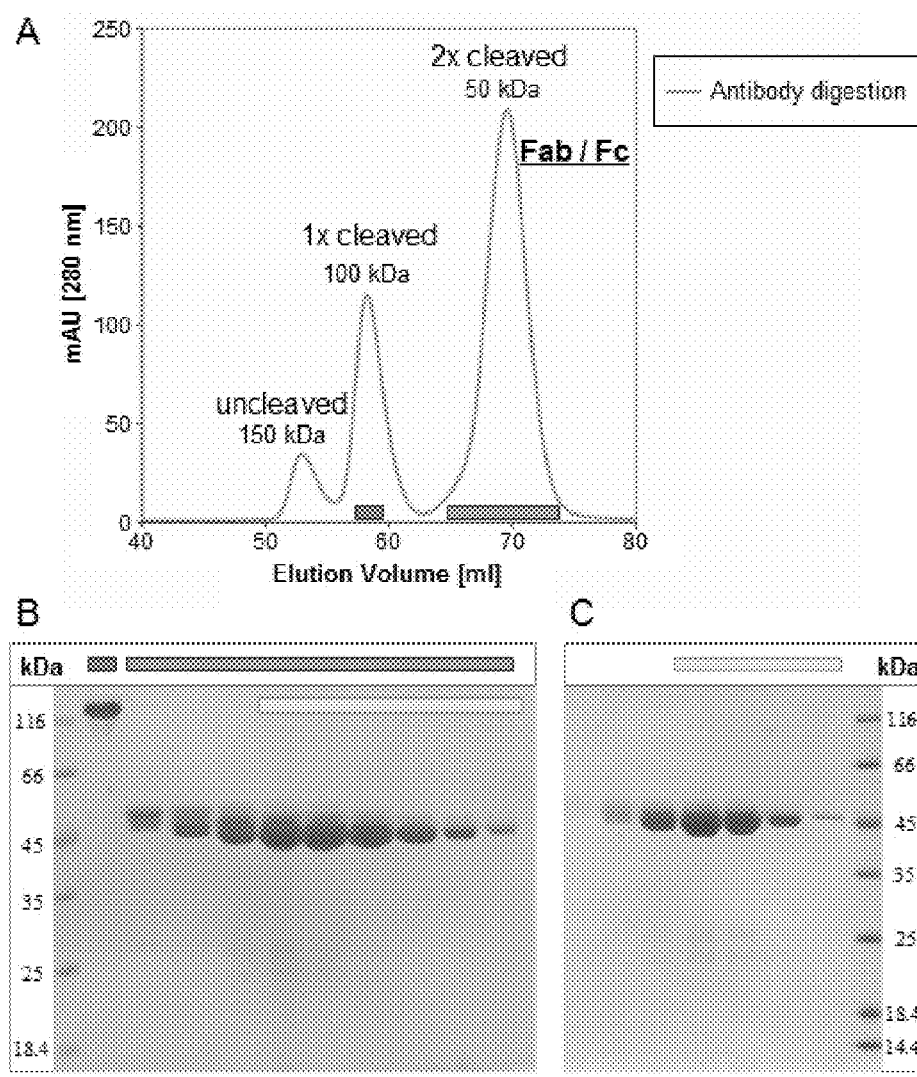
FIGS. 6A-6C show separation and analysis of antibody fragments after papain cleavage. (A) OPN-305 was digested with papain and the products separated by SEC. Fractions indicated with bars were analyzed by SDS-PAGE. (B) SDS gel of complete cleaved antibody (longer top bar) and incomplete cleaved molecules (shorter top bar). Fractions marked by the bottom bar were pooled and separated in a second SEC. (C) SDS-PAGE analysis of fractions of the second SEC. The marked samples (bar) were pooled and used for further experiments. Gel marker: Unstained Protein Molecular Weight Marker (Fermentas).

After cleavage, size-exclusion chromatography (SEC) was performed with the digested sample by which the Fab and Fc fragments (~50 kDa) were separated from the uncleaved (~150 kDa) and incomplete cleaved (~100 kDa) antibody molecules (FIG. 6A). The protein fractions from the SEC (FIG. 6A, green and red bars) were analyzed by SDS-PAGE to confirm the purity of the samples (FIG. 6B). Non-reducing sample conditions were used avoiding reduction of the disulfide bridges between the heavy and light chains to analyze the molecules in their native size. The 1× cleaved antibody has a size of ~100 kDa and runs on the SDS gel above the 116 kDa marker band (FIG. 6Error! Reference source not found.B, red bar), which may be caused by the elongated shape of the molecule. Analyzing the Fab/Fc fraction by SDS-PAGE, one expected two close bands around 50 kDa, with the Fc fragment (54 kDa) running slightly higher than the Fab fraction (48 kDa). In fact four bands can be observed on the gel (FIG. 6B, green bar), suggesting that papain cleaves the antibody at two different contiguous positions. Because the Fab sample should be as homogenous as possible for crystallization experiments, the fractions from the SEC containing the two Fab variants (the two lower bands in FIG. 6B, yellow bar) were pooled and run on a second SEC. Its fractions were again analyzed by SDS-PAGE (FIG. 6C). Only the second half of the fractions containing most of the smaller Fab variant were pooled and used for further experiments (FIG. 6C). Using this strategy, ~80% of the bigger Fab variant could be separated. To further determine the exact mass of the two Fab variants, mass spectrometry experiments were performed.

Identification of Fab Fragments by Mass Spectrometry

First, peptide mass fingerprinting of SDS gel samples from each the bigger and the smaller Fab fragment was performed, which in both cases could clearly identify peptides belonging to the constant Fab region of light chain (Ig kappa chain C, Uniprot entry: P01834) and heavy chain (Ig gamma-4 chain C, Uniprot entry: P01861) of a human IgG4 antibody.

Figure 7:
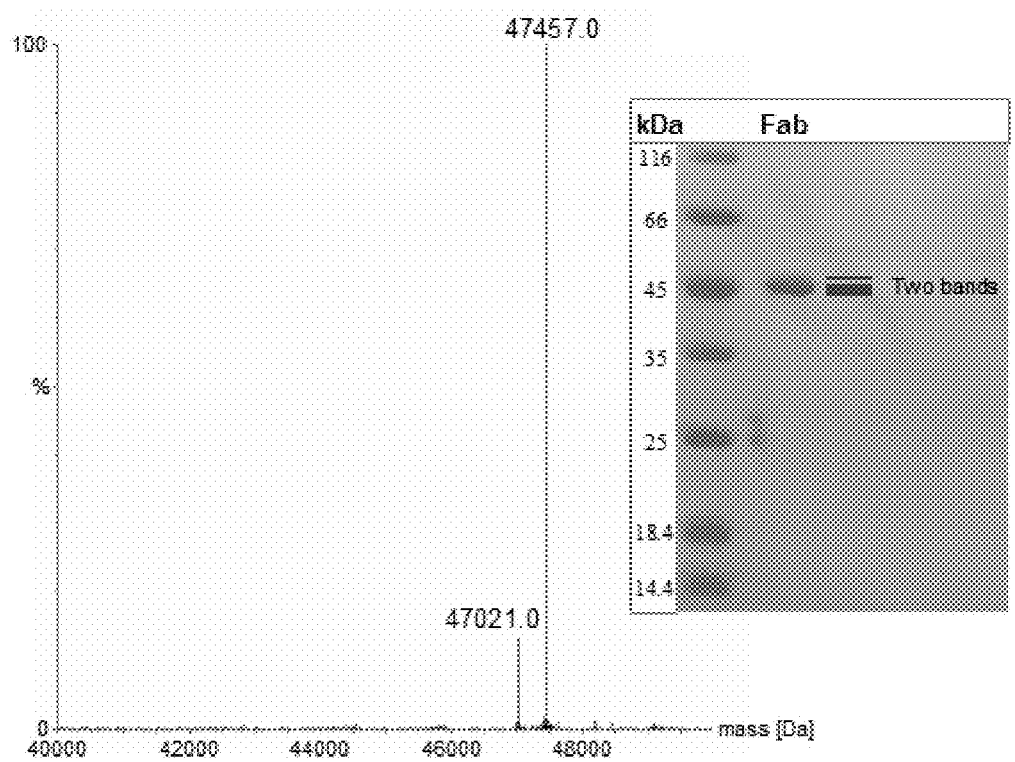
FIG. 7 shows mass spectrometry of Fab. Electrospray ionization mass spectrometry of Fab in solution. The sample was analyzed by SDS-PAGE prior to MS. Two Fab variants of different sizes (47021 Da and 47457 Da) were identified. Gel marker: Unstained Protein Molecular Weight Marker (Fermentas).

Electrospray ionization mass spectrometry (ESI-MS) was then performed with the Fab sample to determine the exact molecular weight of the compounds in solution. Two different proteins with masses of 47021 Da and 47457 Da were identified (FIG. 7). Based on the known amino acid sequences of light chain ($Fab_{light}$) and heavy chain ($Fab_{heavy}$) of OPN-305 it is possible to calculate the two papain cleavage sites within the heavy chain. A mass of 47457 Da corresponds to $Fab_{light}$+$Fab_{heavy}$ $Q^1$-$G^{221}$, whereas the 436 Da shorter variant matches with $Fab_{light}$+$Fab_{heavy}$ $Q^1$-$G^{217}$. The calculation and heavy chain sequence is shown in FIG. 8.

According to the peak height (=signal intensity) in the ESI-MS experiment (FIG. 7), the percentage of total protein amount between the two variants in solution is approximately 15% $Fab_{light}/Fab_{heavy}$ $Q^1$-$E^{217}$ versus 85% $Fab_{light}/Fab_{heavy}$ $Q^1$-$G^{221}$.

Generation and Purification of the TLR2/Fab Complex

Figure 9:
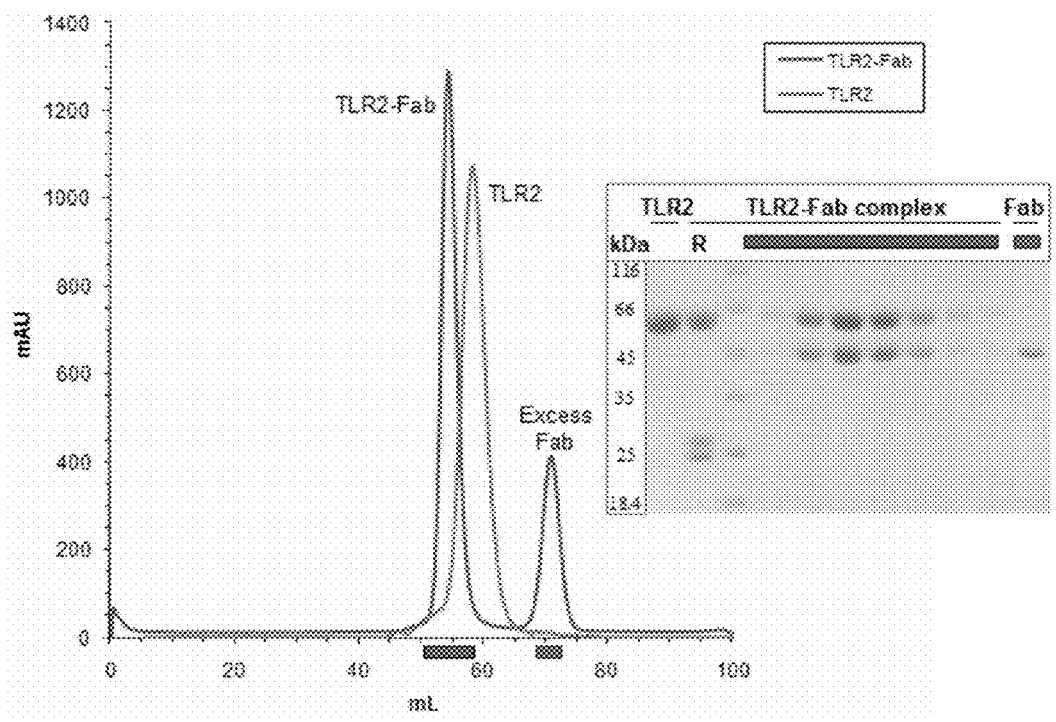
FIG. 9 shows peak shift during SEC between TLR2 and TLR2/Fab. Overlay of size exclusion chromatographs of TLR2/Fab and TLR2. Peak shift indicates complex formation. Fractions of the TLR2/Fab curve were analyzed by SDS-PAGE. TLR2/Fab complex fractions (longer bar) and excess Fab (shorter bar) are marked. Sample of TLR2 and non-reduced sample of TLR2/Fab (R) are shown for comparison. Gel marker: Unstained Protein Molecular Weight Marker (Fermentas).

Purified TLR2 and Fab were incubated in a molar ratio of 2:1 and analyzed by SEC (FIG. 9). The overlay of TLR2/Fab SEC (first curve in FIG. 9) with a curve of TLR2 without Fab (second curve in FIG. 9) shows a clear peak shift indicating the generation of the complex, which has a higher molecular weight than TLR2 alone. The applied TLR2 was completely bound to Fab molecules in a 1:1 complex, excess Fab fragments and residual Fc fragments could be separated. The SEC fractions were analyzed by SDS-PAGE. Fractions of the complex peak (FIG. 9, first bar) show two peaks on the gel (upper band is TLR2, lower band is Fab under non-reduced conditions), whereas the excess Fab peak (FIG. 9, second bar) resulted in a single band. For comparison, the SDS-gel also shows a sample of TLR2 (first lane) and of the complex under reduced conditions (second lane), leading to the separation of Fab into two chains about 25 kDa.

Native PAGE

Figure 10:
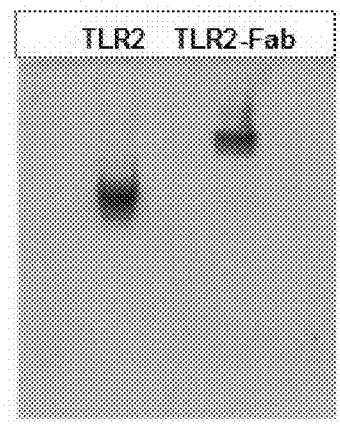
FIG. 10 shows native PAGE analysis of TLR2/Fab. Comparison of TLR2 monomer with TLR2-Fab under native conditions. The complex migrated slower through the pores of the gel due to its size.

To verify the complex formation, native PAGE was performed, which allows the analysis of proteins in their folded, non-denatured form. In native PAGE, the gel mobility depends on the ratio of electric charge to hydrodynamic friction (Arakawa et al. 2006). Thus, two proteins with different sizes and shapes like TLR2 and TLR2/Fab are expected to migrate differently through the gel. As seen in FIG. 10, the migration path of the complex is shorter than that of the TLR2 monomer, which confirms that the TLR2/Fab complex was successfully generated. The fact that the complex remains stable during the PAGE run is an indication of high affinity of Fab towards TLR2.

Stability of TLR2/Fab

Figure 11:
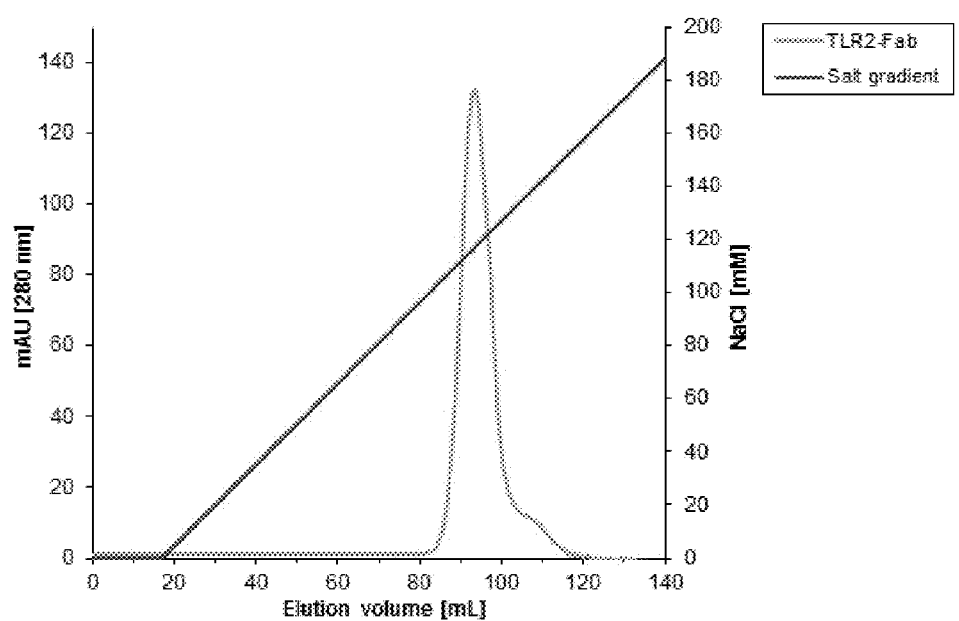
FIG. 11 AEC of TLR2/Fab. TLR2-Fab from the SEC was separated by AEC. The proteins were eluted from column dependent by their negative charge by applying a salt gradient from 0 mM to 200 mM NaCl (line) and were monitored by measuring the absorption at 280 nm (curve).

To further analyze the quality of the complex, an AEC was performed with TLR2/Fab. The aim was to test whether the complex binds uniformly to the AEC column or if a distribution of peaks would be observed, which would indicate an instable or flexible protein complex. The chromatogram in FIG. 11 shows a homogeneous and sharp peak eluting with buffer containing 120 mM NaCl. Only a small shoulder can be observed at 140 mM salt. The elution time of the main peak and the shoulder is similar to that of the AEC of the TLR2 monomer (FIG. 3), indicating that TLR2/Fab and the TLR2 from the fractions which were chosen initially show a similar binding behaviour to the chromatographic column, and that the protein hasn't changed in terms of stability and folding. For further experiments, the purified complex after SEC was used. During the process of purification, the correct selection of TLR2 fractions after the AEC (FIG. 3) without neighbouring side peaks was the crucial step to obtain a homogenous TLR2, and thus, TLR2/Fab sample.

Negative Stain Electron Microscopy

Electron microscopy (EM) is a commonly used technique to visualize a wide range of biological and inorganic specimens including macromolecules like proteins and protein complexes. In contrast to crystallography, EM is a direct method to observe molecules. In negative stain EM the sample is deposited on a carbon coated grid and then covered with a small drop of an electron-opaque staining solution. The stain fixes the specimen on the grid in random orientations and produces high contrast 'electron micrographs', images of a field of the specimen. By collecting thousands of particle images, one can perform a single-particle reconstruction to obtain the structure of the molecule. If, as in our case, the crystal structures of the single molecules of a complex are solved, it is then possible to dock these structures into the EM density map to gain structural insights into the protein interaction.

Visualization of TLR2/Fab by EM

Figure 12:
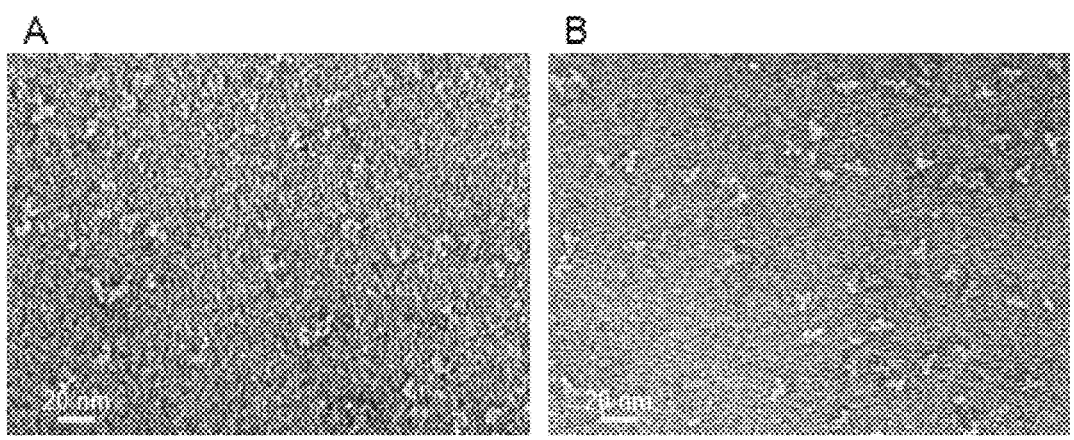
FIGS. 12A-12B show negative stain EM imaging of TLR2 and TLR2/Fab. Visualization of (A) TLR2 and (B) TLR2/Fab complex by negative stain EM.
Figure 13:
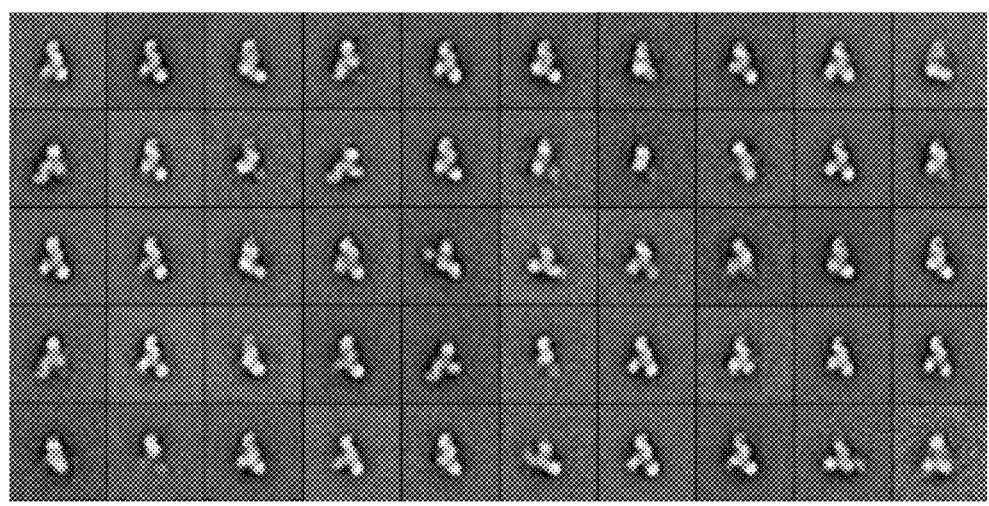
FIG. 13 shows class averages. 5174 particles were classified into 50 classes with identical views. The classes were averaged to obtain high quality particle pictures.

After the TLR2/Fab complex was formed and purified in the experiments described above, the sample was directly used in negative stain EM experiments. A sample with a concentration of 39 nM was deposited on carbon-coated glow-discharged grids and stained with uranyl acetate solution. The particles on the negative stain EM images have a homogenous shape with a length of ≈150 Å and a width of ≈100 Å (FIG. 12, B). The TLR2/Fab particles can be clearly distinguished from EM particles of TLR2, which show the characteristic horseshoe-like shape (FIG. 12, A). In order to perform a reconstruction of a 3D density map numerous steps are required. First it is necessary to collect a large stack of particles with molecules in many different orientations. In total 5174 individual particles were picked from hundreds of EM images using the sparx engine. Mathematical operations were carried out with the software SPIDER to align the particles by reference-free alignment and to classify the particles into 50 classes with identical views. Then averages were computed from the classes to generate particles pictures in high contrast. The class averages are shown in FIG. 13. The averages represent the TLR2/Fab complex in different orientations. Although many of them look similar, which indicates that a majority of the particles were fixed to the grids in a preferred orientation, there is also distinct variation present in the classes, a prerequisite for a 3D reconstruction. Most of the averages have a sharp particle boundary and flat background which indicates high consistency of the particles within the class.

Reconstruction of the 3D Density Map

Figure 14:
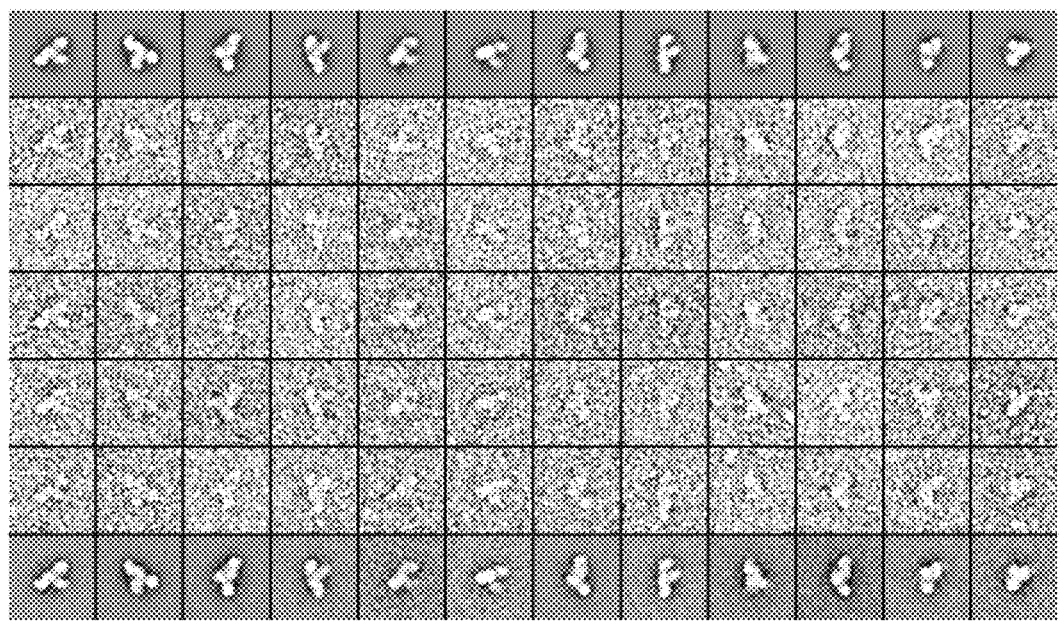
FIG. 14 shows reference-based alignment method. Reference-projections and particle alignment of the 39th back-projection. The first line shows 12 of the 86 2D reference projections generated from the previous iteration. Lines 2-6 are representing particles, which were aligned to the references in the first line. After alignment, each particle set of a reference was averaged, shown in the last line.
Figure 15:
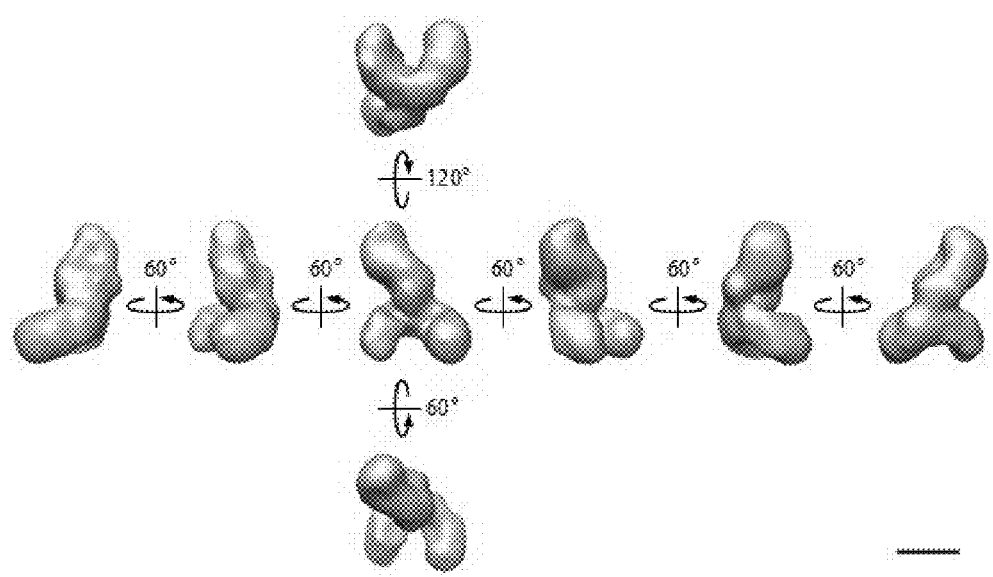
FIG. 15 shows a density map of TLR2/Fab filtered to 21.7 Å. The density map is rotated about the vertical axis in 60° steps or about 120° and 60° around the horizontal axis in reference to the centered third structure from the left, as indicated by the curved arrows. The complex structure is composed of a horseshoe-like domain and an elongated domain sitting lateral and centered on the top of the "horseshoe". Scale bar is 50 Å.

The "good" class averages were used to manually build a first 3D model in PyMOL (Schrödinger, USA) by placing the crystal structures of mTLR2 (PDB entry: 2Z81) and an IgG antibody Fab fragment (PDB entry: 2NY7) according to the particle shape seen in the averages. This model was used as a reference for single-particle reconstruction using the reference-based alignment method. First, a set of 86 2D reference projections was generated from the 3D reference model. Then, the particle stack was aligned against the 2D projections and transformations were applied according to the alignment parameters. The aligned particle images were used to create an initial 3D reconstruction, of which again 86 reference projections were generated. In total 39 iterations of back-projections were performed to refine the alignment parameters (FIG. 14). By comparison the generated reference-projections and the averages calculated from the particles, which were aligned to each projection, a high consistency can be observed. This demonstrates the correctness of the projections and the high quality of alignment. The back-projection method resulted in the 3D density map presented in FIG. 15.

To calculate the resolution of the 3D reconstruction, the particle data was split into two equal sets prior to the back-projection procedure, and the two resulting half-reconstruction were compared. Using the Fourier shell correlation (FSC)=0.5 criteria, a resolution of 21.7 Å was calculated from the FSC curve of the final density map. The structure of the complex is ≈130 Å×90 Å×70 Å in size and composed of a nearly planar horseshoe-like domain on which lateral and in the centre a second domain is situated, with angles of 15° and 40° tilted from the perpendicular axis on the horseshoe-like plane.

Analysis of TLR2/OPN-305 Interaction—Docking of TLR2/Fab into the Density Map

Figure 16:
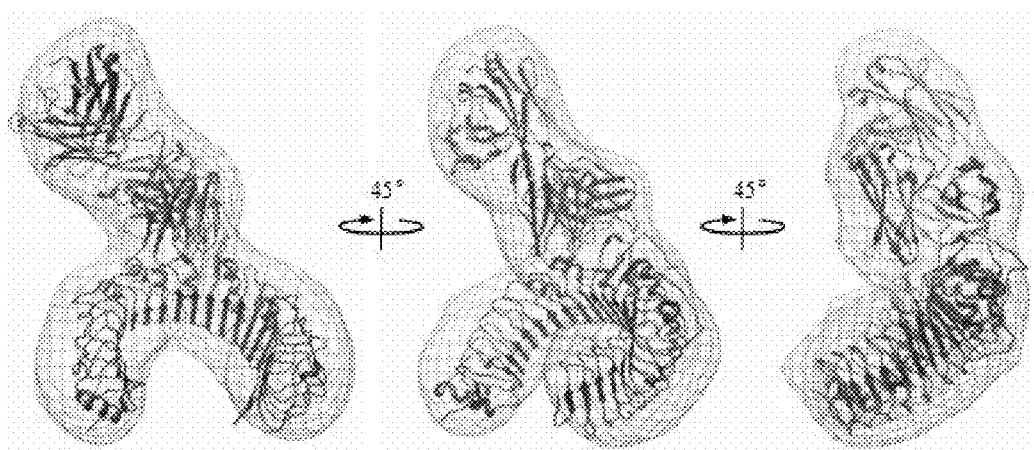
FIG. 16 shows representation of the complex molecules within the EM density map. The structure is rotated about the vertical axis in 45° steps. TLR2 is shown in green (bottom), Fab heavy chain in brown (top), and Fab light chain in blue (top).

To identify the interaction area between TLR2 and OPN-305 Fab, crystal structures of mTLR2 and antibody were fitted into the EM density map (FIG. 16). Like all TLRs, the ECD of mTLR2 is composed of multiple consecutive LRRs forming a solenoid structure, which is forced into a curved configuration because of closely packed β sheets on the concave surface leading to a horseshoe-like shape. The 3D reconstruction shows a similar structural feature, and the crystal structure of mTLR2 ECD (PDB entry: 2Z81) could be docked into the curved structure of the EM map (FIG. 16, green bottom molecule). An antibody Fab fragment is composed of two amino acid chains, heavy and light chain, each containing one constant and one variable part. Although the crystal structure of OPN-305 is not solved, antibodies are very consistent in structure, apart from the 6 CDRs which are responsible for antigen recognition. 3D structure prediction was used to model the variable domain of OPN-305, especially to obtain a structure with correct CDR sequences and length. The crystal structure of an IgG antibody with an identical constant domain sequence to OPN-305 was then used as a framework (pdb entry: 2NY7) and its variable domain was replaced by the modelled OPN-305 variable domain. The Fab domain was placed into the EM map in the density lateral on the centre of TLR2, facing with the variable domain and its antigen binding site towards the TLR2 surface (FIG. 16, blue: light chain; brown: heavy chain).

Analysis of TLR2/OPN-305 Interaction—OPN-305 Blocks the TLR2 Dimerization Site

Figure 17:
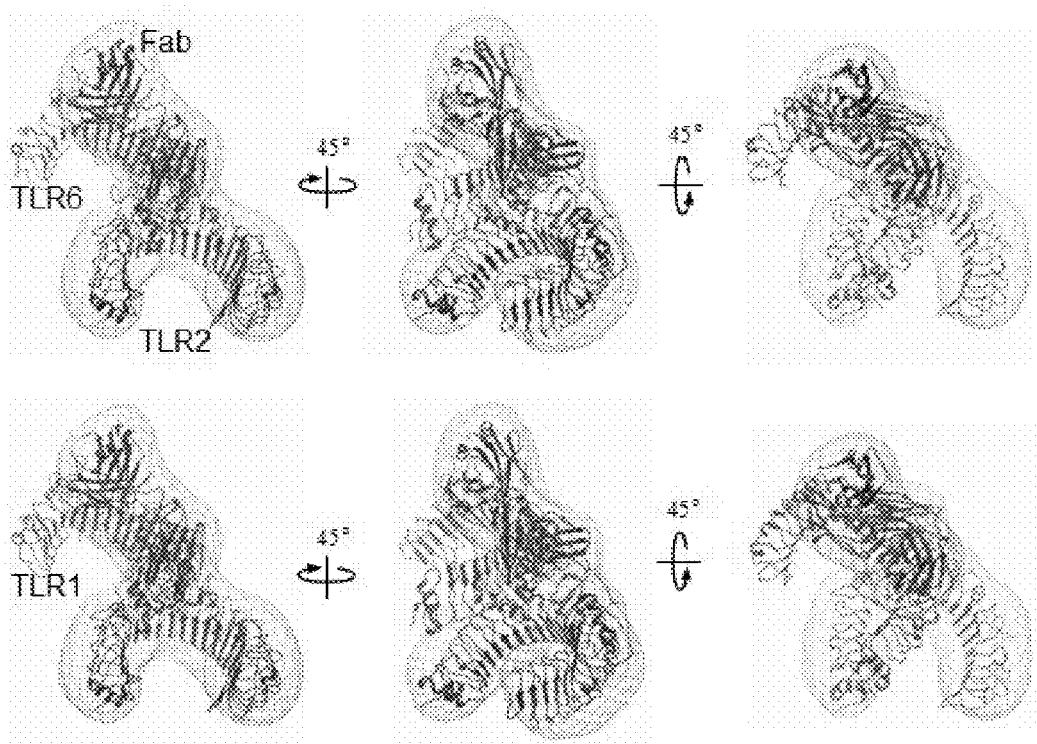
FIG. 17 shows TLR2 dimerization is blocked by OPN-305. Overlapping of TLR1 and TLR6 bound to TLR2 with OPN-305. The structure is rotated for 45° about the vertical and horizontal axis (in reference to the left structure). TLR2 is shown in green (bottom), Fab heavy chain in brown, and Fab light chain in blue, TLR1 in violet, and TLR6 in red.

After TLR2 and Fab were docked into the EM density, the structure was overlapped with the structures of TLR1 and TLR6, bound to TLR2 in the same orientation as they do in the TLR2/TLR1 and TLR2/TLR6 complexes (FIG. 17). The overlapping clearly illustrates that OPN-305 binds to TLR2 in the same region as TLR1 and TLR6. The antibody blocks the dimerization site, and thus blocks TLR1 and TLR6 of forming heterodimers with TLR2.

Analysis of the Epitope

Figure 18:
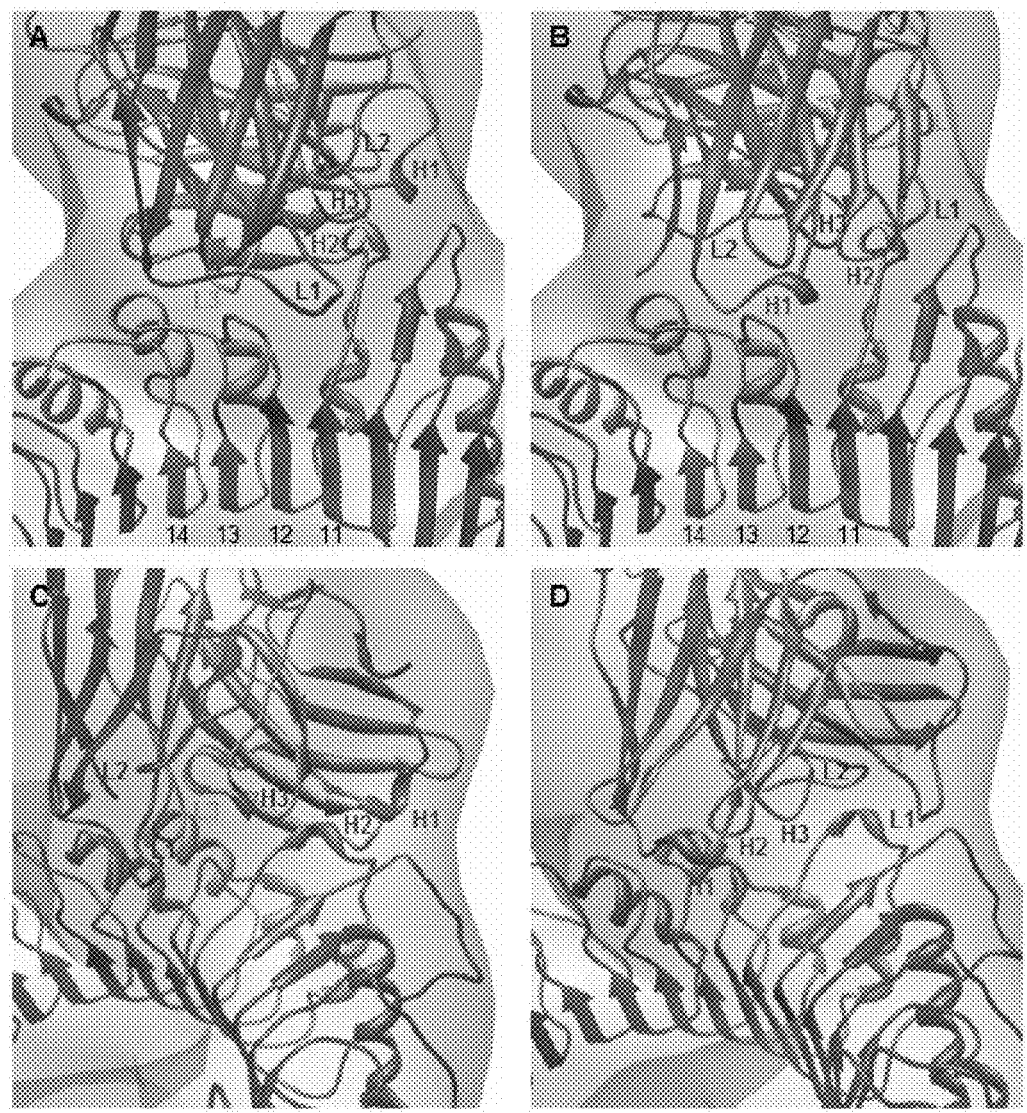
FIGS. 18A-18D show binding of Fab to TLR2 in two theoretical orientations. Fab orientations #1 (A and C) and #2 (B and D) in two views. TLR2 is highlighted in green, the leucin rich repeats 11 to 14 of TLR2 in orange, the Fab heavy chain in brown, and the Fab light chain in blue. The six CDRs are coloured individually and are termed H1-H3 (CDRs of the heavy chain) and L1-L3 (CDRs of the light chain).

Due to the high structural homology of light and heavy chain, the quasi 2-fold symmetry of Fab allows two orientations of the domain within the density, turned at 180° to each other. The biggest differences between light and heavy chain of a Fab fragment lie in the six CDRs of the variable region, because each CDR has a different sequence and length and thus, a different conformation. Although one of the two possible orientations shows a slightly better fitting into the density, both Fab orientations were analyzed and compared to optimally predict possible surface interactions (FIG. 18). Looking at the binding interface reveals that in both possible orientations the lateral surface loops of the LRRs 11-14 are mainly involved in the interaction with the CDRs of OPN-305. Especially the exposed loop of LRR11 plays a crucial role in the recognition, as it is in close distance to at least 3 CDRs of the heavy and light chain.

Crystallization of the Complex

Figure 20:
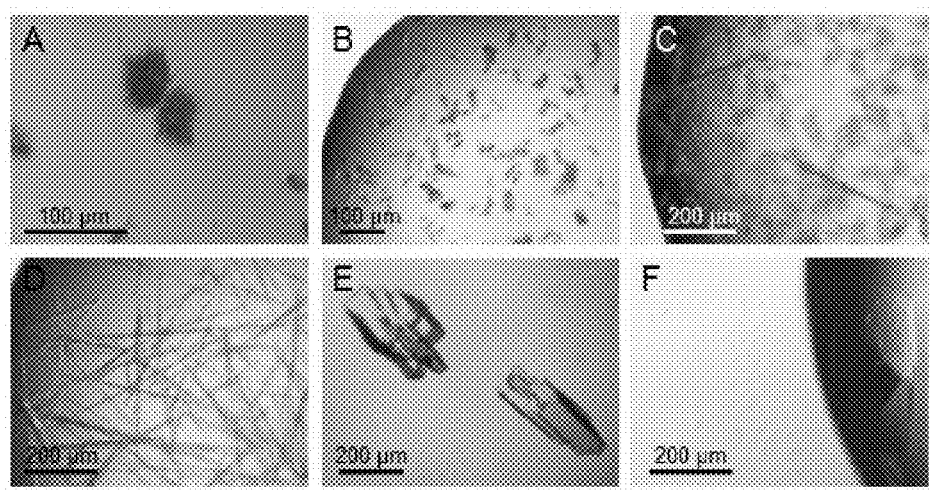
FIGS. 20A-20F show crystals of TLR2/Fab. Different shapes of crystals from different stages of optimization are shown. (A) Initial needle clusters from cross-seeding. (B) Reproduction of needle clusters. (C) Sporadic single needle crystals within clusters. (D) Thin and long needles. (E) Crystals grown together. (F) Single crystal.
Figure 21:
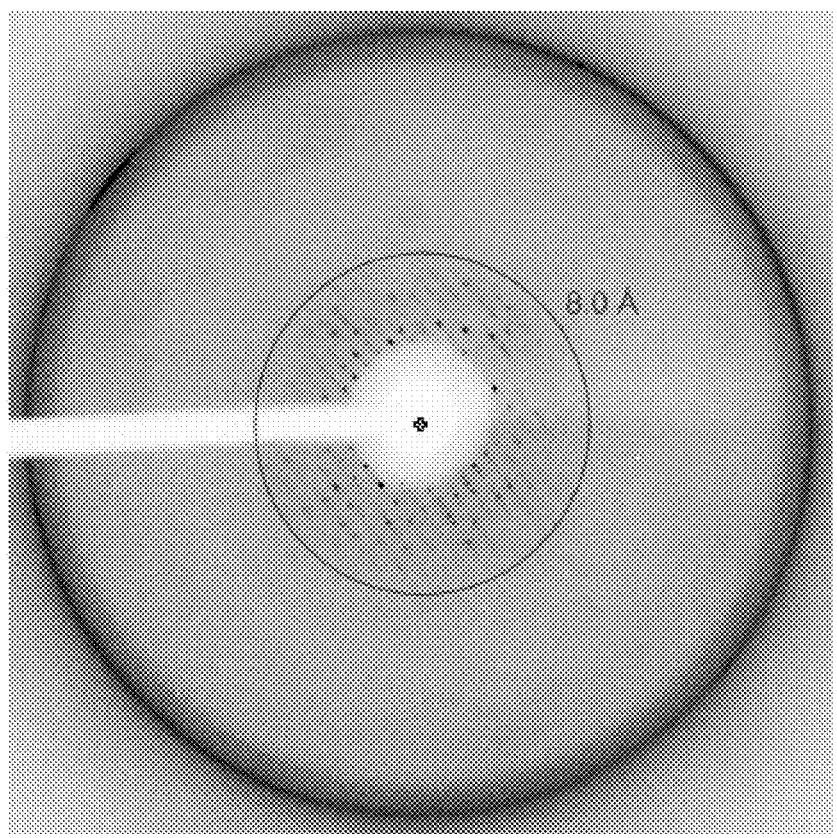
FIG. 21 shows the diffraction pattern of TLR2/Fab crystal. Diffraction of TLR2/Fab (crystal see FIG. 20, F). The beam origin is indicated by a green cross; the red circle marks the resolution shell of 8.0 Å.
Figure 22:
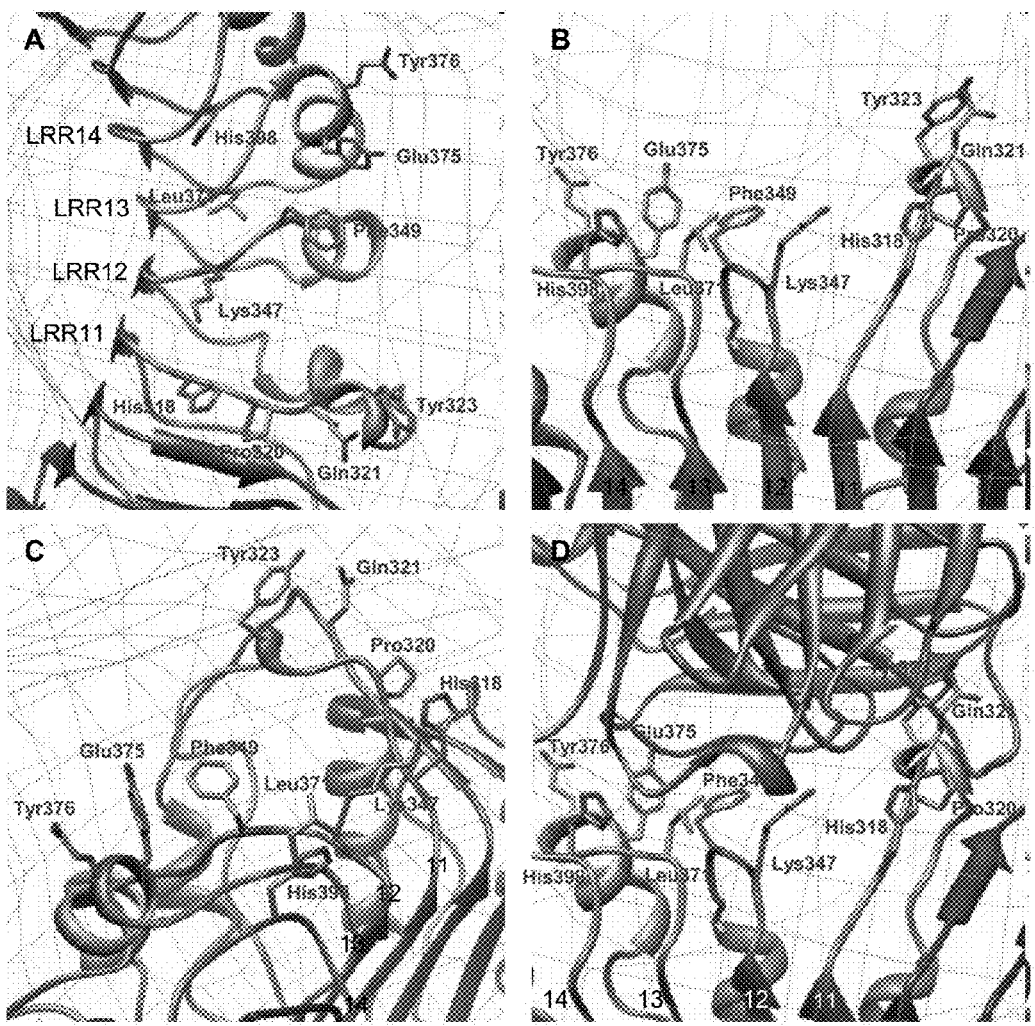
FIGS. 22A-22D show the exposed surface residues of mTLR2. The TLR2 residues on the surface of LRRs 11-14 with side chains exposed towards the exterior are indicated in grey and labelled. In total 10 residues could be identified which are most probably involved in antibody interaction. (A) Top view, (B) front view, (C) side view and (D) top view with Fab heavy chain and light chain.

The TLR2/Fab complex used for crystallization was shown to be pure and stable in solution in the experiments described above. In addition, no aggregates could be seen on EM images. More than 1000 crystallization setups were carried out at different protein concentrations (5-20 mg/mL). Initial protein crystals of TLR2/Fab (FIG. 20) were obtained at 20 mg/mL by cross-seeding with Internalin C crystals (provided by Lilia Polle, UWC, Cape Town, South Africa) under one distinct condition. These needle clusters were then used for optimization by microseeding to obtain single and bigger crystals suitable for diffraction experiments. Crystals with different growth characteristics were produced, but initially optimization trials still resulted in needle clusters (FIG. 20, B+C) or single, but very fragile and thin needles (FIG. 20, C+D). One attempt to increase the crystal dimensions and quality is to increase the solubility of the protein, and thus, to reduce the crystal growth speed by adding higher salt concentrations and/or glycerol. Higher salt concentrations resulted in much bigger (~300 μm=200 μm) crystals (FIG. 20, E). The best crystal of TLR2/Fab was obtained in presence of glycerole (FIG. 20, F) at a protein concentration of 11 mg/mL. The single, big crystal (~500 μm×200 μm×200 μm) resulted in weak and smeared diffraction spots to ~8 Å on a rotating anode (FIG. 21). Indexing of the diffraction images resulted in the crystal space group C222 (C-centred orthorhombic) with unit cell dimensions of a=176 Å, b=310 Å, and c=97 Å. Although a full dataset was collected, structure determination using molecular replacement was not successful. The weak, isomorphous diffraction pattern and a high mosaicity of the crystal of >3° leaded to bad scaling parameters and to a small number of only 3700 unique reflections usable for processing.

Heterogeneous glycosylation of TLR2 can have a negative effect on the homogenicity of the protein crystals and thus on their diffraction quality. Therefore, besides untreated TLR2, TLR2 was deglycosylated prior to complex formation and crystallization. Another approach was to add PNGase F directly to the crystallization condition. Crystallization setups, however, did not lead to crystal improvements, but are still under observation.

Other unsuccessful approaches were the incubation of the crystallization setups at 4° C., the adding of additives (Additive Screen, Hampton Research, California, USA) to the crystallization conditions or the usage of TLR2/Fab anion-exchange samples rather than size exclusion fractions.

Although it was not possible to solve the crystal structure of TLR2-Fab, the obtained crystals are a promising starting point for further investigations of structural features of this complex (Dr. Ezenwa James Onyemata, UWC, Cape Town, South Africa).

All documents referred to in this specification are herein incorporated by reference. Modifications and variations to the described embodiments of the inventions will be apparent to those skilled in the art, without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A screening method or assay for identifying a binding member which specifically binds to Toll-like receptor 2 (TLR2) and antagonises TLR2 activation and signalling, the screening method comprising the steps of:
bringing a candidate compound into contact with a polypeptide fragment of Toll-like receptor 2 (TLR2), the polypeptide fragment comprising:
amino acid residues His318, Pro320, Tyr323, Lys347, Phe349, Leu371, Glu375, Tyr376 and His398 of TLR2 as defined in SEQ ID NO:3 or SEQ ID NO:4,
wherein said polypeptide fragment of TLR2 is a polypeptide fragment of TLR2 other than the extracellular domain of TLR2 comprising amino acid residues of SEQ ID NO:7 or SEQ ID NO:8,
wherein the amino acid residues His318, Pro320, Tyr323, Lys347, Phe349, Leu371, Glu375, Tyr376 and His398 form a functional epitope in said polypeptide fragment, wherein binding of the functional epitope by the binding member antagonises TLR2 activation and signalling and wherein the functional epitope is bound by TLR2 antagonistic antibody T2.5 and a humanised version thereof designated OPN-305, and
wherein the polypeptide fragment comprises less than about 200 amino acid residues of TLR2; and
assessing binding between the candidate compound and the polypeptide fragment,
wherein binding between the candidate compound and the polypeptide fragment identifies the candidate compound as an antagonist of TLR2 activation and signalling.

2. The screening method as claimed in claim 1 wherein the polypeptide fragment comprises amino acid residues His318, Pro320, Tyr323, Lys347, Phe349, Leu371, Glu375, Tyr376 and His398 of murine TLR2 as defined in SEQ ID NO:4 and said amino acid residues form the functional epitope.

3. The screening method as claimed in claim 1 wherein the polypeptide fragment comprises amino acid residues His318, Pro320, Tyr323, Lys347, Phe349, Leu371, Glu375, Tyr376 and His398 of human TLR2 as defined in SEQ ID NO:3 and said amino acid residues form the functional epitope.

4. The screening method as claimed in claim 1 wherein the polypeptide fragment consists essentially of SEQ ID NO:5 or SEQ ID NO:6 or a sequence which has at least 85% sequence identity with SEQ ID NO:5 or SEQ ID NO:6.

5. The screening method as claimed in claim 1 wherein the polypeptide fragment comprises less than about 150 amino acid residues of TLR2.

6. The screening method as claimed in claim 5 wherein the polypeptide fragment comprises less than about 102 amino acid residues of TLR2.

7. The screening method as claimed in claim 1 wherein the polypeptide fragment consists essentially of amino acid residues Thr311 to Thr411 of SEQ ID NO:3 or SEQ ID NO:4 or a sequence which has at least 85% sequence identity with the amino acid residues Thr311 to Thr411 of SEQ ID NO:3 or SEQ ID NO:4.

8. The screening method as claimed in claim 1 wherein the polypeptide fragment consists essentially of amino acid residues Leu317 to His398 of SEQ ID NO:3 or SEQ ID NO:4 or a sequence which has at least 85% sequence identity with the amino acid residues Leu317 to His398 of SEQ ID NO:3 or SEQ ID NO:4.

9. The screening method as claimed in claim 1 wherein the polypeptide fragment consists essentially of amino acid residues His318 to His398 of SEQ ID NO:3 or SEQ ID NO:4 or a sequence which has at least 85% sequence identity with the amino acid residues His318 to His398 of SEQ ID NO:3 or SEQ ID NO:4.

10. The screening method as claimed in claim 1 wherein the polypeptide fragment consists essentially of leucine rich repeat regions 11 to 14 of TLR2 or a sequence which has at least 85% sequence identity with the leucine rich repeat regions 11 to 14 of TLR2.

11. The screening method as claimed in claim 1 wherein the polypeptide fragment is a fragment of human TLR2 or murine TLR2.

* * * * *